US008383107B2

(12) United States Patent
Muruganandam et al.

(10) Patent No.: US 8,383,107 B2
(45) Date of Patent: *Feb. 26, 2013

(54) SINGLE DOMAIN BRAIN-TARGETING ANTIBODY FRAGMENTS DERIVED FROM LLAMA ANTIBODIES

(75) Inventors: Arumugam Muruganandam, Bangalore (IN); Jamshid Tanha, Ottawa (CA); Saran Narang, Ottawa (CA); Danica Stanimirovic, Orleans (CA)

(73) Assignee: National Research Council of Canada, Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/052,441

(22) Filed: Mar. 21, 2011

(65) Prior Publication Data

US 2011/0171720 A1 Jul. 14, 2011

Related U.S. Application Data

(63) Continuation of application No. 10/450,036, filed as application No. PCT/CA01/00783 on May 25, 2001, now Pat. No. 7,943,129.

(60) Provisional application No. 60/207,234, filed on May 26, 2000, provisional application No. 60/263,108, filed on Jan. 22, 2001.

(51) Int. Cl.
*A61K 39/395* (2006.01)
*A61K 39/00* (2006.01)
*A61K 39/38* (2006.01)
*C07K 14/00* (2006.01)
*C07K 17/00* (2006.01)

(52) U.S. Cl. .................. 424/130.1; 424/184.1; 530/350
(58) Field of Classification Search ............... 424/130.1, 424/184.1; 530/350
See application file for complete search history.

(56) References Cited

U.S. PATENT DOCUMENTS

| 5,182,107 A | 1/1993 | Friden |
| 5,759,808 A | 6/1998 | Casterman et al. |
| 5,792,457 A | 8/1998 | Tuomanen et al. |
| 5,800,988 A | 9/1998 | Casterman et al. |
| 5,840,526 A | 11/1998 | Casterman et al. |
| 5,855,885 A | 1/1999 | Chiswell et al. |
| 5,874,541 A | 2/1999 | Casterman et al. |
| 6,172,197 B1 | 1/2001 | McCafferty et al. |
| 6,399,763 B1 | 6/2002 | Frenken et al. |
| 2004/0161738 A1 | 8/2004 | Muruganandam et al. |

FOREIGN PATENT DOCUMENTS

| EP | 0 739 981 A | 10/1996 |
| EP | 0 934 953 A | 8/1999 |
| WO | WO 94/04678 | 3/1994 |
| WO | WO 99/37681 | 7/1999 |
| WO | WO 99/42077 A | 8/1999 |
| WO | WO 00/43507 A | 7/2000 |

OTHER PUBLICATIONS

Abbas et al., *Cellular and Molecular Immunology* 1997; 3rd ed., Pub. by W.B. Saunders Company, pp. 38 and 58 only.
Abhinandan et al., *Molecular Immunology* 2008; 45:3832-3839.
Blier et al., "A Limited Number of B Cell Lineages Generates the Heterogeneity of a Secondary Immune Response," *The Journal of Immunology*, vol. 139, 3996-4006, No. 12, Dec. 15, 1987.
Cai et al., "A melanoma-specific $V_H$ antibody cloned from a fusion phage library of a vaccinated melanoma patient," *Proc. Natl. Acad. Sci. USA*, vol. 93, 6280-6285, Jun. 1996.
Crews et al., "A Single $V_H$ Gene Segment Encodes the Immune Response to Phosphorylcholine: Somatic Mutation Is Correlated with the Class of the Antibody," *Cell*, vol. 25, 59-66, Jul. 1981.
Davies et al., *Protein Engineering* 1996; 9(6):531-537.
Davies et al., "'Camelising' human antibody fragments: NMR studies on VH domains," *FEBS Letters* 339 (1994) 285-290.
Davies, J. et al., "Antibody VH domains as small recognition units," *Bio/Technology*, 13: 475-479 (1995).
Decanniere et al., "A single-domain antibody fragment in complex with RNase A: non-canonical loop structures and nanomolar affinity using two CDR loops," *Structure*, 1999, vol. 7, No. 4, 361-370.
Desmyter et al., "Crystal structure of a camel single-domain $V_H$ antibody fragment in complex with lysozyme," *Nature Structural Biology*, vol. 3, No. 9, Sep. 1996, 803-811.
Dübel, Stefan (Editor); *Handbook of Therapeutic Antibodies*; vol. 1: Technologies; ISBN: 978-3-527-31453-9; Jan. 2007; pp. 97-98.
Fan, Z. et al., "Three-dimensional Structure of an Fv from a Human IgM Immunoglobulin," *J. Mol. Biol.* 1992; 228:188-207.
Ghahroudi et al., "Selection and identification of single domain antibody fragments from camel heavy-chain antibodies," *FEBS Letters* 414 (1997) 521-526.
Hamers-Casterman et al., "Naturally occurring antibodies devoid of light chains," *Nature*, vol. 363, 446-448, Jun. 3, 1993.
Hoogenboom, H. et al., "Antibody phage display technology and its applications," *Immunotechnology*, 4: 1-20 (1998).
Krebber, C. et al., "Co-selection of cognate antibody-antigen pairs by selectively-infective phages," *FEBS*, 337: 227-231 (1995).
Lauwereys, M. et al., "Potent enzyme inhibitors derived from dromedary heavy-chain antibodies," *The Embo Journal*, 17: 3512-3520 (1998).

(Continued)

*Primary Examiner* — Amber D. Steele
(74) *Attorney, Agent, or Firm* — Wolf, Greenfield & Sacks, P.C.

(57) ABSTRACT

A phage-displayed library of llama single heavy domain antibodies (sdAbs) was enriched for species that selectively bind to and are internalized by human cerebromicrovascular endothelial cells (HCEC). From the enriched library, two sdAbs were selected, sequenced, subcloned, and expressed as fusion proteins with c-myc-$His_5$ tags ($His_5$ is SEQ ID NO:101). Similarly as phage-displayed sdAbs, these soluble tagged sdAbs were shown to selectively bind to HCEC and to transmigrate across in vitro human blood-brain barrier (BBB) model. In contrast to an unrelated llama sdAb, these sdAbs were also detected in the brain after i.v. injection into mice. These small (~13 kDa) antibody fragments have essential characteristics of brain-specific delivery vectors and can be used to facilitate drug transport across the BBB.

22 Claims, 11 Drawing Sheets

OTHER PUBLICATIONS

Li, J.Y. et al., "Genetically engineered brain drug delivery vectors: cloning, expression and in vivo application of an anti-transferrin receptor single chain antibody-streptavidin fusion gene and protein," *Protein Engineering* 1999; 12(9):787-796.

Morrison, S.L. et al., "Genetically engineered antibodies and their application to brain delivery," *Advanced Drug Delivery Reviews* 1995; 15:147-175.

Muyldermans et al., "Sequence and structure of $V_H$ domain from naturally occurring camel heavy chain immunoglobulins lacking light chains," *Protein Engineering*, vol. 7, No. 9, 1129-1135, 1994.

Muyldermans, S., "Single domain camel antibodies: current status," *Reviews in Molecular Biotechnology* 2001; 74:277-302.

Nguyen, V. et al., "Camel-heavy chain antibodies: diverse germline VHH and specific mechanisms enlarge the antigen-binding repertoire," *The Embo Journal*, 19: 921-930 (2000).

Nguyen, V.K. et al., "The Specific Variable Domain of Camel Heavy-chain Antibodies is Encoded in the Germline," *J. Mol. Biol.* 1998; 275:413-418.

Reiter, Y. et al., "An Antibody Single-domain Phage Display Library of a Native Heavy Chain Variable Region: Isolation of Functional Single-domain VH Molecules with a Unique Interface," *J. Mol. Biol.* 1999; 290:685-698.

Sampath, A. et al., "Versatile vectors for direct cloning and ligation-independent cloning of PCT-amplified fragments for surface display on filamentous bacteriophages," *Gene*, 190: 5-10 (1997).

Sternberger, N.H. et al., "Blood-brain barrier protein recognized by monoclonal antibody," *Proc. Natl. Acad. Sci. USA* Nov. 1987; 84(22):8169-8173.

Tomlinson et al., "The Repertoire of Human Germline $V_H$ Sequences Reveals about Fifty Groups of $V_H$ Segments with Different Hypervariable Loops," *J. Mol. Biol.* (1992) 227, 776-798.

Vu et al., *Molecular Immunology* 1997; 34:1121-1131.

Ward et al., "Binding activities of a repertoire of single immunoglobulin variable domains secreted from *Escherichia coli*," *Nature*, vol. 341, Oct. 12, 1989, 544-546.

Stanimirovic et al., "Angiotensin II-Induced Fluid Phase Endocytosis in Human Cerebromicrovascular Endothelial Cells Is Regulated by the Inositol-Phosphate Signaling Pathway," Journal of Cellular Physiology, vol. 169, (1966): 455-467.

SEQUENCE LISTING

<160> NUMBER OF SEQ ID NOS: 101

<210> SEQ ID NO 1
<211> LENGTH: 10
<212> TYPE: PRT

<213> ORGANISM: Lama glama

<400> SEQUENCE: 1

Gly Phe Thr Phe Ser Ser Tyr Tyr Met Ser
1               5                   10

<210> SEQ ID NO 2
<211> LENGTH: 10
<212> TYPE: PRT
<213> ORGANISM: Lama glama

<400> SEQUENCE: 2

Gly Arg Thr Phe Ser Asn Tyr His Met Gly
1               5                   10

<210> SEQ ID NO 3
<211> LENGTH: 10
<212> TYPE: PRT
<213> ORGANISM: Lama glama

<400> SEQUENCE: 3

Gly Arg Ile Phe Ser Asn Ala Ala Met Gly
1               5                   10

<210> SEQ ID NO 4
<211> LENGTH: 10
<212> TYPE: PRT
<213> ORGANISM: Lama glama

<400> SEQUENCE: 4

Arg Ser Ile Phe Ser Ile Asn Thr Leu Gly
1               5                   10

<210> SEQ ID NO 5
<211> LENGTH: 10
<212> TYPE: PRT
<213> ORGANISM: Lama glama

<400> SEQUENCE: 5

Gly Arg Ser Phe Ser Thr Tyr Arg Val Gly
1               5                   10

<210> SEQ ID NO 6
<211> LENGTH: 10
<212> TYPE: PRT
<213> ORGANISM: Lama glama

<400> SEQUENCE: 6

Gly Asn Thr Ile Ser Gly Tyr Ala Thr Gly
1               5                   10

<210> SEQ ID NO 7
<211> LENGTH: 10
<212> TYPE: PRT
<213> ORGANISM: Lama glama

<400> SEQUENCE: 7

Gly Gly Ser Phe Ser Asn Tyr Asn Met Gly
1               5                   10

<210> SEQ ID NO 8
<211> LENGTH: 10
<212> TYPE: PRT
<213> ORGANISM: Lama glama

<400> SEQUENCE: 8

-continued

Gly Arg Ile Pro Arg Asn Tyr Pro Ile Gly
1               5                   10

<210> SEQ ID NO 9
<211> LENGTH: 10
<212> TYPE: PRT
<213> ORGANISM: Lama glama

<400> SEQUENCE: 9

Gly Glu Ser Ile Ala Ser Phe Asn Leu Gly
1               5                   10

<210> SEQ ID NO 10
<211> LENGTH: 10
<212> TYPE: PRT
<213> ORGANISM: Lama glama

<400> SEQUENCE: 10

Gly Arg Thr Phe Ser Ser Val Ser Met Gly
1               5                   10

<210> SEQ ID NO 11
<211> LENGTH: 10
<212> TYPE: PRT
<213> ORGANISM: Lama glama

<400> SEQUENCE: 11

Gly Leu Thr Phe Gly Asp Tyr Ala Met Gly
1               5                   10

<210> SEQ ID NO 12
<211> LENGTH: 10
<212> TYPE: PRT
<213> ORGANISM: Lama glama

<400> SEQUENCE: 12

Gly Arg Thr Phe Ser Ser Val Thr Met Gly
1               5                   10

<210> SEQ ID NO 13
<211> LENGTH: 10
<212> TYPE: PRT
<213> ORGANISM: Lama glama

<400> SEQUENCE: 13

Gly Arg Thr Phe Ser Arg Phe Ala Met Gly
1               5                   10

<210> SEQ ID NO 14
<211> LENGTH: 10
<212> TYPE: PRT
<213> ORGANISM: Lama glama

<400> SEQUENCE: 14

Gly Ser Ile Phe Ser Glu Ser Ala Met Gly
1               5                   10

<210> SEQ ID NO 15
<211> LENGTH: 10
<212> TYPE: PRT
<213> ORGANISM: Lama glama

<400> SEQUENCE: 15

Gly Arg Thr Phe Ser Ser Asp Ala Met Gly
1               5                   10

-continued

<210> SEQ ID NO 16
<211> LENGTH: 10
<212> TYPE: PRT
<213> ORGANISM: Lama glama

<400> SEQUENCE: 16

Gly Phe Thr Phe Ser Asn Phe Trp Met Gly
1               5                   10

<210> SEQ ID NO 17
<211> LENGTH: 10
<212> TYPE: PRT
<213> ORGANISM: Lama glama

<400> SEQUENCE: 17

Gly Arg Ser Phe Asn His Tyr Ile Met Gly
1               5                   10

<210> SEQ ID NO 18
<211> LENGTH: 10
<212> TYPE: PRT
<213> ORGANISM: Lama glama

<400> SEQUENCE: 18

Gly Leu Pro Phe Ser Thr Tyr Ser Met Gly
1               5                   10

<210> SEQ ID NO 19
<211> LENGTH: 10
<212> TYPE: PRT
<213> ORGANISM: Lama glama

<400> SEQUENCE: 19

Gly Arg Thr Phe Ser Thr Tyr Thr Met Gly
1               5                   10

<210> SEQ ID NO 20
<211> LENGTH: 10
<212> TYPE: PRT
<213> ORGANISM: Lama glama

<400> SEQUENCE: 20

Gly Tyr Thr Phe Ser Ser His Ala Met Gly
1               5                   10

<210> SEQ ID NO 21
<211> LENGTH: 10
<212> TYPE: PRT
<213> ORGANISM: Lama glama

<400> SEQUENCE: 21

Gly Phe Arg Phe Ala Glu Tyr Ala Ile Gly
1               5                   10

<210> SEQ ID NO 22
<211> LENGTH: 10
<212> TYPE: PRT
<213> ORGANISM: Lama glama

<400> SEQUENCE: 22

Gly Arg Thr Phe Ser Arg Phe Ala Met Gly
1               5                   10

<210> SEQ ID NO 23

```
<211> LENGTH: 10
<212> TYPE: PRT
<213> ORGANISM: Lama glama

<400> SEQUENCE: 23

Gly Phe Thr Phe Val Asp Tyr Ser Met Thr
 1               5                  10

<210> SEQ ID NO 24
<211> LENGTH: 10
<212> TYPE: PRT
<213> ORGANISM: Lama glama

<400> SEQUENCE: 24

Gly Phe Thr Phe Ser Asn Tyr Tyr Met Tyr
 1               5                  10

<210> SEQ ID NO 25
<211> LENGTH: 10
<212> TYPE: PRT
<213> ORGANISM: Lama glama

<400> SEQUENCE: 25

Gly Leu Thr Phe Ser Ser Tyr Val Met Gly
 1               5                  10

<210> SEQ ID NO 26
<211> LENGTH: 10
<212> TYPE: PRT
<213> ORGANISM: Lama glama

<400> SEQUENCE: 26

Gly Gly Thr Phe Thr Asp Tyr Ala Met Gly
 1               5                  10

<210> SEQ ID NO 27
<211> LENGTH: 10
<212> TYPE: PRT
<213> ORGANISM: Lama glama

<400> SEQUENCE: 27

Gly Phe Thr Phe Ser Asn Tyr Tyr Met Tyr
 1               5                  10

<210> SEQ ID NO 28
<211> LENGTH: 10
<212> TYPE: PRT
<213> ORGANISM: Lama glama

<400> SEQUENCE: 28

Gly Asn Thr Ile Ser Asp Tyr Ala Thr Gly
 1               5                  10

<210> SEQ ID NO 29
<211> LENGTH: 17
<212> TYPE: PRT
<213> ORGANISM: Lama glama

<400> SEQUENCE: 29

Gly Ile Tyr Ser Asp Ser Ser Ile Thr Ala Tyr Ala Asp Ser Val Lys
 1               5                  10                  15

Gly

<210> SEQ ID NO 30
<211> LENGTH: 17
```

```
<212> TYPE: PRT
<213> ORGANISM: Lama glama

<400> SEQUENCE: 30

Ser Ile Lys Trp Ser Gly Gly Asn Thr Tyr Tyr Ala Asp Ser Val Lys
 1               5                  10                  15
Gly

<210> SEQ ID NO 31
<211> LENGTH: 17
<212> TYPE: PRT
<213> ORGANISM: Lama glama

<400> SEQUENCE: 31

Ala Ile Arg Trp Ser Asp Gly Asn Thr Tyr Tyr Ala Asp Ser Val Lys
 1               5                  10                  15
Gly

<210> SEQ ID NO 32
<211> LENGTH: 16
<212> TYPE: PRT
<213> ORGANISM: Lama glama

<400> SEQUENCE: 32

Trp Ile Thr Ser Gly Gly Ala Thr Tyr Tyr Ala Asp Ser Met Lys Gly
 1               5                  10                  15

<210> SEQ ID NO 33
<211> LENGTH: 17
<212> TYPE: PRT
<213> ORGANISM: Lama glama

<400> SEQUENCE: 33

Gly Ile Asn Trp Asn Gly Val Lys Thr Arg Tyr Ser Asp Ser Met Asn
 1               5                  10                  15
Asp

<210> SEQ ID NO 34
<211> LENGTH: 17
<212> TYPE: PRT
<213> ORGANISM: Lama glama

<400> SEQUENCE: 34

Ala Val Thr Trp Ser Gly Tyr Ser Val Tyr Tyr Ala Lys Ser Pro Lys
 1               5                  10                  15
Gly

<210> SEQ ID NO 35
<211> LENGTH: 17
<212> TYPE: PRT
<213> ORGANISM: Lama glama

<400> SEQUENCE: 35

Gly Ile Gly Trp Ser Gly Gly Arg Ile Ile Val Ala Asp Ser Val Lys
 1               5                  10                  15
Gly

<210> SEQ ID NO 36
<211> LENGTH: 17
<212> TYPE: PRT
<213> ORGANISM: Lama glama

<400> SEQUENCE: 36
```

```
Gly Ile Ser Trp Thr Ser Gly Thr Thr Tyr Phe Ala Asp Ser Val Lys
  1               5                  10                  15
Gly
```

<210> SEQ ID NO 37
<211> LENGTH: 17
<212> TYPE: PRT
<213> ORGANISM: Lama glama

<400> SEQUENCE: 37

```
Ala Val Ser Arg Thr Gly Glu Thr Thr Asp Tyr Ala Asp Ala Val Lys
  1               5                  10                  15
Gly
```

<210> SEQ ID NO 38
<211> LENGTH: 17
<212> TYPE: PRT
<213> ORGANISM: Lama glama

<400> SEQUENCE: 38

```
Ala Ile Asn Trp Arg Gly Val Ser Thr Tyr Tyr Ala Asp Ser Val Lys
  1               5                  10                  15
Gly
```

<210> SEQ ID NO 39
<211> LENGTH: 17
<212> TYPE: PRT
<213> ORGANISM: Lama glama

<400> SEQUENCE: 39

```
Thr Ile Ser Arg Ile Gly Ser Thr Thr Tyr Tyr Ala Asp Ser Val Lys
  1               5                  10                  15
Gly
```

<210> SEQ ID NO 40
<211> LENGTH: 17
<212> TYPE: PRT
<213> ORGANISM: Lama glama

<400> SEQUENCE: 40

```
Ala Met Thr Arg Asn Ser Gly Ser Thr Tyr Tyr Ala Asp Ser Val Lys
  1               5                  10                  15
Gly
```

<210> SEQ ID NO 41
<211> LENGTH: 17
<212> TYPE: PRT
<213> ORGANISM: Lama glama

<400> SEQUENCE: 41

```
Ala Ile Ser Trp Ser Gly Gly Thr Thr Tyr Gly Ala Asp Ser Ala Lys
  1               5                  10                  15
Gly
```

<210> SEQ ID NO 42
<211> LENGTH: 16
<212> TYPE: PRT
<213> ORGANISM: Lama glama

<400> SEQUENCE: 42

```
Ala Ile Thr Leu Asp Gly Arg Thr Asn Tyr Ala Tyr Tyr Ala Glu Gly
```

```
<210> SEQ ID NO 43
<211> LENGTH: 17
<212> TYPE: PRT
<213> ORGANISM: Lama glama

<400> SEQUENCE: 43

Ala Ile Ser Trp Ser Gly Gly Ser Thr Tyr Tyr Ala Asp Ser Val Lys
 1               5                  10                  15

Gly

<210> SEQ ID NO 44
<211> LENGTH: 17
<212> TYPE: PRT
<213> ORGANISM: Lama glama

<400> SEQUENCE: 44

Gln Ile Asn Thr Gly Gly Asp Ile Thr Thr Tyr Ser Asp Ser Val Lys
 1               5                  10                  15

Gly

<210> SEQ ID NO 45
<211> LENGTH: 17
<212> TYPE: PRT
<213> ORGANISM: Lama glama

<400> SEQUENCE: 45

Ser Ile Asp Trp Asn Ser Gly Arg Thr Asn Tyr Ala Asp Ser Val Lys
 1               5                  10                  15

Gly

<210> SEQ ID NO 46
<211> LENGTH: 17
<212> TYPE: PRT
<213> ORGANISM: Lama glama

<400> SEQUENCE: 46

Val Ile Gly Gly Gly Gly Asn Thr Tyr His Ala Ala Asp Ser Leu Lys
 1               5                  10                  15

Asp

<210> SEQ ID NO 47
<211> LENGTH: 17
<212> TYPE: PRT
<213> ORGANISM: Lama glama

<400> SEQUENCE: 47

Ala Ile Ser Arg Asn Ser Val Gly Thr Tyr Tyr Arg Asp Ser Val Lys
 1               5                  10                  15

Gly

<210> SEQ ID NO 48
<211> LENGTH: 17
<212> TYPE: PRT
<213> ORGANISM: Lama glama

<400> SEQUENCE: 48

Ala Ile Ser Ala Ser Gly Gly Asn Gln Tyr Tyr Lys Tyr Phe Ala Lys
 1               5                  10                  15

Gly
```

```
<210> SEQ ID NO 49
<211> LENGTH: 17
<212> TYPE: PRT
<213> ORGANISM: Lama glama

<400> SEQUENCE: 49

Tyr Ile Ser Thr Ser Asp Lys Thr Thr Tyr Tyr Ser Asp Phe Ala Glu
 1               5                  10                  15
Gly

<210> SEQ ID NO 50
<211> LENGTH: 17
<212> TYPE: PRT
<213> ORGANISM: Lama glama

<400> SEQUENCE: 50

Ala Ile Ser Trp Ser Gly Gly Thr Ala Tyr Gly Ala Asp Ser Ala Lys
 1               5                  10                  15
Gly

<210> SEQ ID NO 51
<211> LENGTH: 17
<212> TYPE: PRT
<213> ORGANISM: Lama glama

<400> SEQUENCE: 51

Ala Ile Asn Trp Asn Gly Arg Leu Thr Tyr Tyr Ala Glu Ser Met Lys
 1               5                  10                  15
Gly

<210> SEQ ID NO 52
<211> LENGTH: 17
<212> TYPE: PRT
<213> ORGANISM: Lama glama

<400> SEQUENCE: 52

Met Val Asn Thr Gly Gly Gly Gly Thr Arg Tyr Ala Asp Ser Val Arg
 1               5                  10                  15
Gly

<210> SEQ ID NO 53
<211> LENGTH: 17
<212> TYPE: PRT
<213> ORGANISM: Lama glama

<400> SEQUENCE: 53

Ala Ile Ile Thr Ser Gly Arg Ser Thr Tyr Tyr Ala Asp Ser Val Lys
 1               5                  10                  15
Gly

<210> SEQ ID NO 54
<211> LENGTH: 17
<212> TYPE: PRT
<213> ORGANISM: Lama glama

<400> SEQUENCE: 54

Ala Ile Asn Trp Gly Gly Tyr Ser Thr Tyr Tyr Ser Asp Ala Val Lys
 1               5                  10                  15
Gly

<210> SEQ ID NO 55
```

```
<211> LENGTH: 17
<212> TYPE: PRT
<213> ORGANISM: Lama glama

<400> SEQUENCE: 55

Met Val Asn Thr Gly Gly Gly Thr Arg Tyr Ala Asp Ser Val Arg
 1               5                  10                  15

Gly

<210> SEQ ID NO 56
<211> LENGTH: 17
<212> TYPE: PRT
<213> ORGANISM: Lama glama

<400> SEQUENCE: 56

Ser Ile Gly Arg Arg Thr Gly Trp Gln Val Tyr Ser Asp Ser Val Lys
 1               5                  10                  15

Gly

<210> SEQ ID NO 57
<211> LENGTH: 12
<212> TYPE: PRT
<213> ORGANISM: Lama glama

<400> SEQUENCE: 57

Met Val Met Gly Pro Ala Ala Thr Gly Tyr Glu Tyr
 1               5                  10

<210> SEQ ID NO 58
<211> LENGTH: 17
<212> TYPE: PRT
<213> ORGANISM: Lama glama

<400> SEQUENCE: 58

Gly Ser Lys Tyr Gly Gly Ser Trp Ser Arg Ser Gln Asp Ala Tyr Asn
 1               5                  10                  15

Tyr

<210> SEQ ID NO 59
<211> LENGTH: 17
<212> TYPE: PRT
<213> ORGANISM: Lama glama

<400> SEQUENCE: 59

Gly Ile Gly Thr Phe Gly Ser Ser Trp Thr Arg Ala Asp Arg Tyr Arg
 1               5                  10                  15

Tyr

<210> SEQ ID NO 60
<211> LENGTH: 6
<212> TYPE: PRT
<213> ORGANISM: Lama glama

<400> SEQUENCE: 60

Arg Val Pro Leu Asp Tyr
 1               5

<210> SEQ ID NO 61
<211> LENGTH: 16
<212> TYPE: PRT
<213> ORGANISM: Lama glama

<400> SEQUENCE: 61
```

```
Asp Gln Arg Phe Asp Gly Asp Asp Trp Ser Pro Ser Ala Phe Thr Arg
1               5                   10                  15
```

<210> SEQ ID NO 62
<211> LENGTH: 16
<212> TYPE: PRT
<213> ORGANISM: Lama glama

<400> SEQUENCE: 62

```
Val Phe Val Arg Thr Ala Gly Val Pro Thr Leu Gly Glu Tyr Asp Tyr
1               5                   10                  15
```

<210> SEQ ID NO 63

<400> SEQUENCE: 63

000

<210> SEQ ID NO 64
<211> LENGTH: 20
<212> TYPE: PRT
<213> ORGANISM: Lama glama

<400> SEQUENCE: 64

```
Ser Glu Arg Asp Phe Tyr Thr Arg Asn Tyr Tyr Phe Thr Phe Glu Ser
1               5                   10                  15

Leu Tyr Asp Tyr
            20
```

<210> SEQ ID NO 65
<211> LENGTH: 17
<212> TYPE: PRT
<213> ORGANISM: Lama glama

<400> SEQUENCE: 65

```
Asp Tyr Asn Leu Gly Thr Phe Val Thr Arg Lys Asp Ser Met Tyr Asp
1               5                   10                  15

Phe
```

<210> SEQ ID NO 66
<211> LENGTH: 15
<212> TYPE: PRT
<213> ORGANISM: Lama glama

<400> SEQUENCE: 66

```
Arg Arg Asn Phe Phe Gly Asn Asn Ser Ala Gly Gln Tyr Ala Tyr
1               5                   10                  15
```

<210> SEQ ID NO 67
<211> LENGTH: 12
<212> TYPE: PRT
<213> ORGANISM: Lama glama

<400> SEQUENCE: 67

```
Ser Arg Tyr Val Leu Lys Tyr Asp Lys Asp Ala Tyr
1               5                   10
```

<210> SEQ ID NO 68
<211> LENGTH: 17
<212> TYPE: PRT
<213> ORGANISM: Lama glama

<400> SEQUENCE: 68

```
Lys Ala Ser Met Tyr Gly Ser Thr Leu Tyr Pro Pro Thr Gly Tyr Asn
1               5                   10                  15
```

Tyr

<210> SEQ ID NO 69
<211> LENGTH: 9
<212> TYPE: PRT
<213> ORGANISM: Lama glama

<400> SEQUENCE: 69

Gly Arg Ala Val Ser Asp Tyr Asp Tyr
1               5

<210> SEQ ID NO 70
<211> LENGTH: 13
<212> TYPE: PRT
<213> ORGANISM: Lama glama

<400> SEQUENCE: 70

Leu Arg Ser Arg Ala Val Met Asp Thr Ile Pro Asn Tyr
1               5                   10

<210> SEQ ID NO 71
<211> LENGTH: 17
<212> TYPE: PRT
<213> ORGANISM: Lama glama

<400> SEQUENCE: 71

Asp Arg Arg Arg Tyr Tyr Ser Gly Ser Tyr Pro Pro Ser Glu Tyr Asp
1               5                   10                  15

Tyr

<210> SEQ ID NO 72
<211> LENGTH: 14
<212> TYPE: PRT
<213> ORGANISM: Lama glama

<400> SEQUENCE: 72

Ala Arg Ser Val Pro Leu Ser Asp Pro Arg Thr Tyr Ser Ser
1               5                   10

<210> SEQ ID NO 73
<211> LENGTH: 14
<212> TYPE: PRT
<213> ORGANISM: Lama glama

<400> SEQUENCE: 73

Ala Ala Ala Ala Ser Thr Leu Val Gly Gly Ser Tyr Asp Tyr
1               5                   10

<210> SEQ ID NO 74
<211> LENGTH: 22
<212> TYPE: PRT
<213> ORGANISM: Lama glama

<400> SEQUENCE: 74

Asp Arg Asp Phe Thr Ile Val Ala Gly Phe Ile Arg Ser Gln Tyr Ser
1               5                   10                  15

Pro Arg Ala Val Glu Tyr
            20

<210> SEQ ID NO 75
<211> LENGTH: 15
<212> TYPE: PRT
<213> ORGANISM: Lama glama

```
<400> SEQUENCE: 75

Asp Pro Met Tyr Gly Arg Ser Val Met Ser Thr Arg Tyr Asn Tyr
1               5                   10                  15

<210> SEQ ID NO 76
<211> LENGTH: 18
<212> TYPE: PRT
<213> ORGANISM: Lama glama

<400> SEQUENCE: 76

Ala Thr Lys Gln Phe Ser Asn Ala Tyr Ser Asp Tyr Val His Asp Tyr
1               5                   10                  15

Asp Tyr

<210> SEQ ID NO 77
<211> LENGTH: 17
<212> TYPE: PRT
<213> ORGANISM: Lama glama

<400> SEQUENCE: 77

Gly Leu Tyr Tyr Ser Asp Tyr Arg Thr Pro Glu Tyr Thr Glu Tyr Val
1               5                   10                  15

His

<210> SEQ ID NO 78
<211> LENGTH: 9
<212> TYPE: PRT
<213> ORGANISM: Lama glama

<400> SEQUENCE: 78

Gly Arg Ala Val Ser Asp Tyr Asp Tyr
1               5

<210> SEQ ID NO 79
<211> LENGTH: 12
<212> TYPE: PRT
<213> ORGANISM: Lama glama

<400> SEQUENCE: 79

Gly Glu Leu Tyr Gly Met Gly Ser Lys His Asp Tyr
1               5                   10

<210> SEQ ID NO 80
<211> LENGTH: 11
<212> TYPE: PRT
<213> ORGANISM: Lama glama

<400> SEQUENCE: 80

Asp Arg Pro Gln Ser Gly Trp Ser Met Asp Tyr
1               5                   10

<210> SEQ ID NO 81
<211> LENGTH: 13
<212> TYPE: PRT
<213> ORGANISM: Lama glama

<400> SEQUENCE: 81

Thr Lys Trp Val Val Arg Arg Pro Ala Asp Tyr Asn Tyr
1               5                   10

<210> SEQ ID NO 82
<211> LENGTH: 12
<212> TYPE: PRT
<213> ORGANISM: Lama glama
```

```
<400> SEQUENCE: 82

Asp Pro Gln Leu Ile Thr Thr Pro Glu Tyr Asn Tyr
 1               5                  10

<210> SEQ ID NO 83
<211> LENGTH: 11
<212> TYPE: PRT
<213> ORGANISM: Lama glama

<400> SEQUENCE: 83

Asp Arg Pro Gln Ser Gly Trp Ser Met Asp Tyr
 1               5                  10

<210> SEQ ID NO 84
<211> LENGTH: 18
<212> TYPE: PRT
<213> ORGANISM: Lama glama

<400> SEQUENCE: 84

Ser Gln Asp Ser Gly Phe Asp Thr Pro Val Thr Glu Ser His Leu Tyr
 1               5                  10                  15

Gly Tyr

<210> SEQ ID NO 85
<211> LENGTH: 122
<212> TYPE: PRT
<213> ORGANISM: Lama glama

<400> SEQUENCE: 85

Glu Val Gln Leu Gln Ala Ser Gly Gly Gly Leu Val Gln Ala Gly Gly
 1               5                  10                  15

Ser Leu Arg Leu Ser Cys Ala Ala Ser Gly Phe Lys Ile Thr His Tyr
            20                  25                  30

Thr Met Gly Trp Phe Arg Gln Ala Pro Gly Lys Glu Arg Glu Phe Val
        35                  40                  45

Ser Arg Ile Thr Trp Gly Gly Asp Asn Thr Phe Tyr Ser Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Asp Tyr Tyr Cys
                85                  90                  95

Ala Ala Gly Ser Thr Ser Thr Ala Thr Pro Leu Arg Val Asp Tyr Trp
            100                 105                 110

Gly Lys Gly Thr Gln Val Thr Val Ser Ser
        115                 120

<210> SEQ ID NO 86
<211> LENGTH: 125
<212> TYPE: PRT
<213> ORGANISM: Lama glama

<400> SEQUENCE: 86

Glu Val Gln Leu Gln Ala Ser Gly Gly Gly Leu Val Gln Ala Gly Gly
 1               5                  10                  15

Gly Leu Arg Leu Ser Cys Ser Ala Ser Val Arg Thr Phe Ser Ile Tyr
            20                  25                  30

Ala Met Gly Trp Phe Arg Gln Ala Pro Gly Lys Glu Arg Glu Phe Val
        35                  40                  45

Ala Gly Ile Asn Arg Ser Gly Asp Val Thr Lys Tyr Ala Asp Phe Val
```

```
                50                  55                  60
Lys Gly Arg Phe Ser Ile Ser Arg Asp Asn Ala Lys Asn Met Val Tyr
 65                  70                  75                  80

Leu Gln Met Asn Ser Leu Lys Pro Glu Asp Thr Ala Leu Tyr Tyr Cys
                 85                  90                  95

Ala Ala Thr Trp Ala Tyr Asp Thr Val Gly Ala Leu Thr Ser Gly Tyr
            100                 105                 110

Asn Phe Trp Gly Gln Gly Thr Gln Val Thr Val Ser Ser
        115                 120                 125

<210> SEQ ID NO 87
<211> LENGTH: 125
<212> TYPE: PRT
<213> ORGANISM: Lama glama

<400> SEQUENCE: 87

Glu Val Gln Leu Gln Ala Ser Gly Gly Gly Leu Val Gln Ala Gly Gly
 1               5                  10                  15

Gly Leu Arg Leu Ser Cys Ser Ala Ser Val Arg Thr Phe Ser Ile Tyr
             20                  25                  30

Ala Ile Gly Trp Phe Arg Gln Ala Pro Gly Lys Glu Arg Glu Phe Val
         35                  40                  45

Ala Gly Ile Asn Arg Ser Gly Asp Val Thr Lys Tyr Ala Asp Phe Val
     50                  55                  60

Lys Gly Arg Phe Ser Ile Ser Arg Asp Asn Ala Lys Asn Met Val Tyr
 65                  70                  75                  80

Leu Gln Met Asn Ser Leu Lys Pro Glu Asp Thr Ala Leu Tyr Tyr Cys
                 85                  90                  95

Ala Ala Thr Trp Ala Tyr Asp Thr Val Gly Ala Leu Thr Ser Gly Tyr
            100                 105                 110

Asn Phe Trp Gly Gln Gly Thr Gln Val Thr Val Ser Ser
        115                 120                 125

<210> SEQ ID NO 88
<211> LENGTH: 21
<212> TYPE: DNA
<213> ORGANISM: Artificial Sequence
<220> FEATURE:
<223> OTHER INFORMATION: primer

<400> SEQUENCE: 88
cgccatcaag gtaccagttg a                                         21

<210> SEQ ID NO 89
<211> LENGTH: 29
<212> TYPE: DNA
<213> ORGANISM: Artificial Sequence
<220> FEATURE:
<223> OTHER INFORMATION: primer

<400> SEQUENCE: 89
gatgtgcagc tgcaggcgtc tggrggagg                                 29

<210> SEQ ID NO 90
<211> LENGTH: 29
<212> TYPE: DNA
<213> ORGANISM: Artificial Sequence
<220> FEATURE:
<223> OTHER INFORMATION: primer

<400> SEQUENCE: 90
```

```
catgaccaca gtgcacagga kgtscagct                                    29
```

<210> SEQ ID NO 91
<211> LENGTH: 33
<212> TYPE: DNA
<213> ORGANISM: Artificial Sequence
<220> FEATURE:
<223> OTHER INFORMATION: primer

<400> SEQUENCE: 91

```
cgattctgcg gccgctgagg agacggtgac ctg                               33
```

<210> SEQ ID NO 92
<211> LENGTH: 35
<212> TYPE: DNA
<213> ORGANISM: Artificial Sequence
<220> FEATURE:
<223> OTHER INFORMATION: primer

<400> SEQUENCE: 92

```
tatgaagaca ccaggccgat gtgcagctgc aggcg                             35
```

<210> SEQ ID NO 93
<211> LENGTH: 27
<212> TYPE: DNA
<213> ORGANISM: Artificial Sequence
<220> FEATURE:
<223> OTHER INFORMATION: primer

<400> SEQUENCE: 93

```
tatggatcct gaggagacgg tgacctg                                      27
```

<210> SEQ ID NO 94
<211> LENGTH: 10
<212> TYPE: PRT
<213> ORGANISM: Lama glama

<400> SEQUENCE: 94

Val Arg Thr Phe Ser Ile Tyr Ala Met Gly
 1               5                  10

<210> SEQ ID NO 95
<211> LENGTH: 10
<212> TYPE: PRT
<213> ORGANISM: Lama glama

<400> SEQUENCE: 95

Gly Phe Lys Ile Thr His Tyr Thr Met Gly
 1               5                  10

<210> SEQ ID NO 96
<211> LENGTH: 10
<212> TYPE: PRT
<213> ORGANISM: Lama glama

<400> SEQUENCE: 96

Val Arg Thr Phe Ser Ile Tyr Ala Ile Gly
 1               5                  10

<210> SEQ ID NO 97
<211> LENGTH: 17
<212> TYPE: PRT
<213> ORGANISM: Lama glama

<400> SEQUENCE: 97

Gly Ile Asn Arg Ser Gly Asp Val Thr Lys Tyr Ala Asp Phe Val Lys

```
1               5                  10                 15
Gly

<210> SEQ ID NO 98
<211> LENGTH: 17
<212> TYPE: PRT
<213> ORGANISM: Lama glama

<400> SEQUENCE: 98

Arg Ile Thr Trp Gly Gly Asp Asn Thr Phe Tyr Ser Asn Ser Val Lys
1               5                   10                  15

Gly

<210> SEQ ID NO 99
<211> LENGTH: 16
<212> TYPE: PRT
<213> ORGANISM: Lama glama

<400> SEQUENCE: 99

Thr Trp Ala Tyr Asp Thr Val Gly Ala Leu Thr Ser Gly Tyr Asn Phe
1               5                   10                  15

<210> SEQ ID NO 100
<211> LENGTH: 13
<212> TYPE: PRT
<213> ORGANISM: Lama glama

<400> SEQUENCE: 100

Gly Ser Thr Ser Thr Ala Thr Pro Leu Arg Val Asp Tyr
1               5                   10

<210> SEQ ID NO 101
<211> LENGTH: 5
<212> TYPE: PRT
<213> ORGANISM: Artificial Sequence
<220> FEATURE:
<223> OTHER INFORMATION: Synthetic His-5 tag

<400> SEQUENCE: 101

His His His His His
1               5
```

SINGLE DOMAIN BRAIN-TARGETING ANTIBODY FRAGMENTS DERIVED FROM LLAMA ANTIBODIES

RELATED APPLICATIONS

This application is a continuation of U.S. patent application Ser. No. 10/450,036, filed Oct. 24, 2003, now U.S. Pat. No. 7,943,129, which is a national stage filing under 35 U.S.C. §371 of international application PCT/CA01/00783, filed May 25, 2001, which was published under PCT Article 21(2) in English; this application also claims the benefit under 35 U.S.C. 119(e) of U.S. provisional application Ser. No. 60/207,234, filed May 26, 2000, and U.S. provisional application Ser. No. 60/263,108, filed Jan. 22, 2001, all of which are incorporated herein by reference.

FIELD OF THE INVENTION

The invention relates to single-domain brain-targeting antibody fragments derived from llama antibodies, in particular to antibody fragments comprising at least a part of the variable heavy domain (VH or $V_HH$) of llama antibodies, which fragments selectively bind to and are internalized by human cerebromicrovascular endothelial cells (HCEC), and transmigrate HCEC monolayer.

BACKGROUND OF THE INVENTION

The immune system in vertebrates provides a defense mechanism against foreign intruders, such as foreign macromolecules or infecting microorganisms. The foreign invaders (antigens), both macromolecules (proteins, polysaccharides, or nucleic acids) and microbes (viruses or bacteria), are recognized through specific binding of the proteins of the host immune system to specific sites on the antigen surface, known as antigenic determinants.

As part of the immune system, B-cells of vertebrate organisms synthesize antigen-recognizing proteins known as antibodies or immunoglobulins (Ig). According to the clonal selection theory, an antigen activates those B-cells of the host organism that have on their surface immunoglobulins that can recognize and bind the antigen. The binding triggers production of a clone of identical B-cells that secrete soluble antigen-binding immunoglobulins into the bloodstream. Antibodies secreted by B-cells bind to foreign material (antigen) to serve as tags or identifiers for such material. Antibody-tagged antigens are then recognized and disposed of by macrophages and other effector cells of the immune system or are directly lysed by a set of nonspecific serum proteins collectively called complement. In this way a small amount of antigen can elicit an amplified and specific immune response that helps to clear the host organism of the source of antigen. Through a complex process of gene splicing combined with additional mutation mechanisms, human B-cells have been estimated to produce a "library" (repertoire) of more than a billion ($10^9$) different antibodies that differ in the composition of their binding sites.

For most vertebrate organisms, including humans and murine species, their antibodies show a common structural pattern which consists of two identical light polypeptide chains and two identical heavy polypeptide chains linked together by disulfide bonds and numerous non-covalent interactions, resulting in a Y-shaped molecule. In humans, there are two different classes (isotypes), X and K, of the light chains, with no known functional distinction between them. The heavy chains have five different isotypes that divide immunoglobulins into five different functional classes (IgG, IgM, IgA, IgD, IgE), each with different effector properties in the elimination of antigen.

Of the above five classes, immunoglobulins of the IgG class are the major type in normal serum of humans and many other species and have the four-chain structure shown schematically in FIG. 1. Each chain of an IgG molecule is divided into domains of about 110 amino acid residues, with the light chains having two such domains and the heavy chains having four. Comparison of amino acid sequences between different IgGs shows that the amino-terminal domain of each chain (both light and heavy) is highly variable, whereas the remaining domains have substantially constant sequences. In other words, the light (L) chains of an IgG molecule are built up from one amino-terminal variable domain (VL) and one carboxy-terminal constant domain (CL), and the heavy (H) chains from one amino-terminal variable domain (VH) followed by three constant domains (CH1, CH2, and CH3).

The variable domains are not uniformly variable throughout their length. Three small regions of a variable domain, known as hypervariable regions (loops) or complementarity determining regions (CDR1, CDR2, and CDR3) show much more variability than the rest of the domain. These regions, which vary in size and sequence among various immunoglobulins, determine the specificity of the antigen-antibody interaction. The specificity of an antibody of the type shown in FIG. 1 is determined by the sequence and size of six hypervariable loops (regions), three in the VL domain and three in the VH domain.

By partial digestion with papain, which cleaves the heavy chains in the hinge region, the IgG molecule can be broken down into two identical Fab fragments (Fragment, antigen binding) and one Fc fragment (Fragment, crystallizes easily). Each Fab fragment comprises one complete light chain (consisting of VL and CL domains) linked by a disulfide bridge and noncovalent interactions to a fragment of the heavy chain consisting of VH and CH1 domains. The Fc fragment comprises CH2 and CH3 domains from both heavy chains, also linked by disulfide bridges and noncovalent interactions. The part of the Fab fragment consisting of variable domains of the light and the heavy chain (VL and VH) is known as Fv fragment (Fragment, variable). In an Fv fragment, the variable domains VL and VH are not covalently bound. In an scFv (single chain Fv) fragment, the VL and VH domains are covalently linked by a short peptide linker (spacer), usually 15 to 20 amino acids long, introduced at the genetic level (see FIG. 2).

scFv fragments are recombinant fusion proteins and are produced by techniques of genetic engineering, by expressing in a suitable host, usually in bacteria, a chimeric gene coding for the fragment. Various other recombinant antibody fragments have been designed to substitute for large intact immunoglobulin molecules (see FIG. 2). Other than scFv fragments, these options include Fab or Fv fragments that are stabilized or covalently linked using various strategies (see, for example, Bird et al., Science, 242, 423-426 (1988); Huston et al., Proc. Natl. Acad. Sci. USA, 85, 5879-5883 (1988); Glockshuber et al., Biochemistry, 29, 1362-1376 (1990); Jung et al., Proteins, 35-47 (1994); Reiter et al., Biochemistry, 5451-5459, 18327-18331 (1994); Young et al., FEBS Lett., 135-139 (1995)). Small antigen-binding fragments of natural antibodies are advantageous for medical applications, for example cancer targeting and imaging, when small antigen-biding molecules are required to penetrate into solid tumors.

Recent advances in gene technology have greatly facilitated the genetic manipulation, production, identification and conjugation of recombinant antibody fragments and broadened the potential utility of antibodies as diagnostic and therapeutic agents. Of particular importance to such applications is the possibility to alter the fine specificity of the antibody binding site, to create small stable antigen-binding fragments, to prepare fusion proteins combining antigen-binding domains with proteins having desired therapeutic properties, for the purpose of immunotargeting, or to "humanize" antibodies of other species, for example murine antibodies (see FIG. 2).

The genetic engineering has also made possible to screen in vitro for antibodies having a predetermined binding specificity. This may be achieved by constructing first a gene library of antibodies or antibody fragments, for example by polymerase chain reaction (PCR)-amplification of cDNA derived from B-lymphocytes using suitable primers, or by in vitro gene synthesis. The gene library may contain sequences corresponding to certain fragments of natural antibodies, or randomized antigen-binding regions, or new combinations of heavy/light chains, thus creating the potential for generating antibodies which could never be obtained from natural sources, for example, antibodies to highly toxic substances or antigens tolerated by the human immune system. By random or designed mutations, the affinity or specificity of the antigen binding can be manipulated, for example, to reach affinities never observed with natural antibodies.

To screen a gene library, which may contain many millions or even billions of different clones, for genes of antibodies having the desired binding specificity, a selection system comparable to that of the immune system is required. Such a selection system can be achieved by inserting the library genes into the genome of microorganisms capable of displaying on their surface the antibody corresponding to the inserted gene, in analogy to the expression of an immunoglobulin antigen receptor on the surface of a B-cell. Microorganisms most frequently used for providing such a display are filamentous bacteriophages, such as fd or M13 phages (phage display). The collection of phage particles having inserted genes of a library of proteins, such as antibodies, and displaying these proteins on the particles' surface is known as a phage display library. The display of the library of antibodies on the surface of phage particles provides a physical link between the antigen-binding function of an antibody and the antibody gene. Using the affinity to a preselected antigen, the whole organism (phage) displaying this affinity can be identified and separated out of billions of non-specific clones, usually through binding to the antigen immobilized on a support, technique usually referred to as panning (see, for example, Scott et al., Science, 249, 386-390 (1990); Winter et al., Annual Rev. Immunology, 12, 433-455 (1994)). Phage clones binding to the antigen can be then amplified and used to produce the specific antibody or antibody fragment in *E. coli* or in other suitable organism.

For naturally occurring antibodies, there are examples that whole heavy chains alone retain a significant binding ability in the absence of light chains. It is also well established, from structural studies, that the CDR3 of the heavy variable domain generally contributes the most to antigen binding, because CDR3 amino acid residues are responsible for most of the surface contact area and molecular interaction with the antigen (Padlan, E. A., Mol. Immunology, 31, 169-217 (1984); Chothia et al., J. Mol. Biol., 196, 904-917 (1987); Chothia et al., J. Mol. Biol., 186, 651-663 (1985)). Less binding activity was observed for light chain. In view of these findings, attempts were made to isolate single VH domains. For example, VH domains were isolated from expression libraries derived from immunized mice (Ward et al., Nature, 341, 544-546 (1989)). In another report, antigen-binding VH domains were rescued from an antibody phage library that was made from a vaccinated patient (Cai et al., Proc Natl. Acad. Sci. USA, 93, 6280-6285 (1996)). Antigen-binding antibody fragments consisting of a single VH domain, known as dAbs or sdAbs (single-domain antibodies), are becoming an attractive alternative to single chain Fv (scFv) fragments. Despite smaller binding surface, their demonstrated affinity is comparable to that demonstrated by scFv fragments (Davies et al., Biotech., 13, 475-479 (1995)). Because of their smaller size, being half of the size of scFvs, sdAbs are amenable to detailed NMR structural studies (Davies et al., FEBS Letters, 339, 285-290 (1994)). Additionally, due to their simpler structure, sdAbs are more stable and have simpler folding properties.

Recently, a new class of antibodies known as heavy chain antibodies (HCA, also referred to as two-chain or two-chain heavy chain antibodies) have been reported in camelids (Hamers-Casterman et al., Nature, 363, 446-448 (1993); see also U.S. Pat. No. 5,759,808; U.S. Pat. No. 5,800,988; U.S. Pat. No. 5,840,526; and U.S. Pat. No. 5,874,541). Compared with conventional four-chain immunoglobulins of IgG-type, which are also produced by camelids, these antibodies lack the light chains and CH1 domains of conventional immunoglobulins. One of the salient features of these naturally occurring heavy chain antibodies is the predominant presence of Glu, Arg and Gly at VL interface positions 44, 45 and 47 (Kabat numbering), respectively, of their variable domain (designated $V_H H$). The same positions in the variable domain of the heavy chain of conventional four-chain antibodies (designated VH) are almost exclusively occupied by Gly, Leu and Trp. These differences are thought to be responsible for the high solubility and stability of camelid HCA variable domain ($V_H H$), as compared with the relative insolubility of VH domain of the conventional four-chain antibodies. Two more salient features of camelid $V_H H$ domains are their comparatively longer CDR3 and high incidence of cysteine pairs in CDRs. It appears that cysteine pairs mediate the formation of a disulfide bridge and are therefore involved in modulating the surface topology of the antibody combining site. In the crystal structure of a camel sdAb-lysozyme complex, a rigid loop protruding from the sdAb and partly stabilized by a CDR disulfide linkage extends out of the combining site and penetrates deeply into the lysozyme active site (Desmyter et al., Nature Struct. Biol., 3, 803-811 (1996)).

More recently, a number of camelid sdAbs phage display libraries have been generated from the $V_H H$ repertoire of camelids immunized with various antigens (Arbabi et al., FEBS Letters, 414, 521-526 (1997); Lauwereys et al., EMBO J., 17, 3512-3520 (1998); Decanniere et al., Structure, 7, 361-370 (1999)). By creating polyclonal libraries, many highly soluble sdAbs with high affinity and specificity have been isolated. However, it has been questioned whether sdAbs with desired affinity and defined conformations can be generated in the absence of prior immunization, i.e., with a naïve library (Lauwereys et al., supra). Immunization of domesticated valuable animals, such as camelids, raises serious ethical implications related to experiments with animals. Moreover, this approach has serious drawbacks because most of the pathogenic antigens cannot be injected into camelids, as this could endanger their lives. Considering the above drawbacks and limitations of the prior art, there exists a strong need for the generation of phage display libraries of sdAb antibody fragments derived from naïve libraries of camelid antibodies, in particular sdAb fragments of camelid heavy chain antibodies, which libraries may become a universal source of sdAbs for in vitro selection against any antigen of interest as a target. By choosing antigen targets located in tissues of therapeutic or diagnostic interest or importance, such libraries may provide new vectors for targeted delivery of therapeutic and diagnostic agents. Of particular interest to the present invention are antibody fragments targeting antigens of the endothelial tissue of the blood-brain barrier (BBB), which fragments may be used for the delivery of therapeutic and diagnostic agents into neuronal tissues.

The effective delivery of molecules into neuronal tissues remains one of the most perplexing challenges facing the pharmaceutical and biotechnology industries. The brain is isolated from the rest of the body by a specialized endothelial tissue known as the blood-brain barrier (BBB). The endothelial cells of the BBB are connected by tight junctions and efficiently prevent many therapeutic compounds from entering the brain. In addition to low rates of vesicular transport, one specific feature of the BBB is the existence of enzymatic barrier(s) and high level(s) of expression of ATP-dependent transporters, including P-glycoprotein (Gottesman et al., Ann. Rev. Biochem., 62, 385-427 (1993); Watanabe, T., Acta Oncol., 34, 235-241 (1995)), which actively degrade/extrude various pharmaceuticals from the brain (Samuels B. L., J. Clin. Pharmacol. Ther., 54, 421-429 (1993). As a result, a plethora of compounds with demonstrated efficacy in vitro cannot be used as brain-targeting pharmaceutical agents in vivo unless appropriate delivery vehicles capable of overcoming the impermeability of the BBB are employed.

Only small (<600 Daltons) and hydrophobic (Pardridge, W. M., Adv. Drug Delivery Reviews, 15, 5-36 (1995)) molecules can easily pass the BBB, a constraint that places enormous restrictions on drug development strategies. Current brain drug delivery practices either employ invasive neurosurgical procedures or non-invasive strategies such as pharmacological methods to facilitate transport of drugs via intercellular or transcellular routes. In addition to invasive and highly limited neurosurgical strategies (e.g., intraventricular drug infusion, cerebral implants) and osmotic BBB opening applied clinically, strategies based on 1) physiological- and 2) pharmacological modulation of BBB permeability are being developed.

Strategies based on physiological approaches to drug delivery through the BBB use pseudonutrients that are substrates for BBB nutrient carrier systems (Pardridge, W. M., supra). At least eight different nutrient transport systems have been identified in cerebromicrovascular endothelial cells (i.e., glucose transporter, the neutral amino-acid carrier, the basic amino acid carrier, the monocarboxylic amino acid carrier, the purine nucleoside transport carrier, the purine base carrier, choline carrier, and glutamate transporter) many of which are being exploited to carry drugs that 'mimic' the respective natural ligands for these transporters into the brain. While this strategy constitutes a clear advance over current alternatives, it is limited by the fact that such drugs will have to compete with endogenous substrates normally transported by these systems.

For the pharmacologically-based strategies, the delivery of small molecules through the BBB include also lipidization approaches and liposomes (Pardridge, W. M., supra). Lipidization of small molecules involves chemical modification of hydrogen bond-forming polar functional groups with apolar functional groups, e.g., O-methylation, or O-acetylation. The alternative approach is to attach free-fatty acyl or cholesterol groups to drugs in order to form more hydrophobic and BBB permeable compounds. The entrapment of various compounds into liposomes has been widely utilized to deliver drugs to various tissues and organs. However, despite many efforts invested into developing liposomal strategies to overcome the BBB, liposomes have, in general, failed to improve the penetration of drug(s) into the brain (Micklus et al., Biochim. Biophys. Acta, 1124, 7-12 (1992); Gennuso et al., Cancer Invest., 11, 118-128 (1993)). In fact, it has been shown that even small liposome vesicles (50 nm) do not undergo significant BBB transport (Micklus et al., supra). Moreover, one novel pharmacological strategy to transiently disrupt the BBB takes advantage of the fact that the activation of specific peptide and/or neurotransmitter receptors expressed on cerebromicrovascular endothelial cells (CEC) leads to transient 'loosening' of the tight junctions maintaining barrier integrity (Black, K. L., Adv. Drug Delivery Reviews, 15, 37-52 (1995)). This strategy, known as receptor-mediated permeabilization, has been successfully used by Alkemes Inc. to deliver anti-tumor drugs into brain tumors by selectively disrupting the blood-tumor barrier with bradykinin $B_2$ receptor agonists (Inamura et al., J. Cerebral Blood Flow Metab., 14, 862-870 (1994)). However, it appears that $B_2$ receptor activation does not affect BBB properties outside the peritumoral areas, and therefore this strategy appears to be ineffective in delivering drugs across the intact BBB (Inamura et al., supra).

The development of efficient ways to deliver large molecules such as peptides, proteins and nucleic acids across the BBB is also crucial to the future success of growth factor- and gene-based therapies to fight disorders of the central nervous system (CNS). The principal strategy currently being pursued to deliver these macromolecules across the BBB is the development of chimeric peptides (Pardridge, W. M., Adv. Drug Delivery Reviews, 15, 109-146 (1995); Boado, R. J., Adv. Drug Delivery Reviews, 15, 73-107 (1995)). This strategy takes advantage of various receptors present on brain capillary endothelium that mediate the transcytosis of essential proteins through the BBB, including transferrin, insulin growth factor and low-density lipoprotein (Friden, P. M., in: The Blood Brain Barrier: Cellular and Molecular Biology (Pardridge, W. M., Ed.), Raven Press, New York, pp. 229-248 (1993)). This process is known as a receptor-mediated endocytosis/transcytosis. Therefore, macromolecule delivery to the brain can potentially be achieved by coupling proteins and nucleic acids to agonist/antibody "vectors" which bind these receptors, allowing absorptive or receptor-mediated transcytosis to bring these compounds to the brain. Proof of principle for this technology has been recently achieved using an anti-transferrin receptor antibody (OX-26) to successfully deliver endorphin, vasoactive intestinal peptide and BDNF into brain tissue in experimental animals (Pardridge, W. M., supra). Similarly, the same antibody has been used to deliver oligonucleotides and plasmid DNA (Boado, R. J., supra) into the brain parenchyma. However, before becoming a useful therapeutic tool, chimeric peptide technology requires further development in the following areas: 1) the discovery of additional suitable vectors expressed on human BBB endothelium; and 2) the development of improved strategies to link vectors to proteins/nucleic acids.

The relative inability of polypeptides and polynucleotides to access the brain is compounded by the fact that even if they were to penetrate the BBB, the transport of these compounds across neuronal cell membranes is extremely low. Even direct intracerebral administration of peptides, antisense oligonucleotides and plasmid DNA often fail to produce the desired therapeutic effect due to minimal diffusion and low uptake of these compounds into neurons and other cells of the CNS. To date, viral vectors have exhibited the highest levels of gene transfer efficiencies. However, the potential advantages offered by non-viral transfection systems, such as the lack of viral gene elements, higher safety and lower immunogenicity, have fueled the development of non-viral alternatives for in vivo gene therapy (Hanania et al., Amer. J. Med., 99, 537-552 (1995); Gregoriadis, G., TIBTECH, 13, 527-537 (1995)). For example, highly efficient in vitro gene transfer capacity has been reported for cationic liposomes (Gao et al., Gene Therapy, 2, 710-722 (1995)), although their eventual utility may be limited by the fact that these "vectors" are quite toxic and are strongly inhibited by serum. More recently, polycationic non-lipid compounds have been shown to achieve superior gene transfer efficiencies in vivo relative to cationic liposome preparations (Goldman et al., Nature Biotechnology, 15, 462-466 (1997)). However, attempts to deliver polypeptides and polynucleotides into neurons by complexing them with liposomes, nanoparticles, and low molecular weight surfactants have been largely disappointing because of the high intrinsic sensitivity of neurons to the toxic effects of such delivery systems (Abbott et al., Mol. Med. Today, 3, 106-113 (1996)). In reality, even if these delivery systems were to effectively deliver drugs across neuronal and glial membranes, the "Achilles heel" remain their incapacity to penetrate the intact BBB. That formidable and persistent problem remains the predominant issue.

It is clear in view of the above that new approaches are necessary to identify and provide vectors capable of transmigrating the BBB barrier and delivering therapeutic or diagnostic molecules to neuronal tissues. The present invention provides such new vectors free of many prior art limitations.

SUMMARY OF THE INVENTION

The present invention has overcome some of the above-discussed prior art limitations by generating a large size (in the order of $10^9$) phage display library of antibody fragments of a non-immunized llama, which fragments comprise at least a part of the variable heavy domain (VH or $V_H$H domain) of llama antibodies. In a preferred embodiment, the fragments consist essentially of the variable heavy domain (VH or $V_H$H) of llama antibodies (sdAb fragments). The library has a number of unique features which distinguish it from similar libraries generated from other camelids.

From this library, sdAb fragments capable of binding selectively to human cerebromicrovascular endothelial cells (HCEC) and of transmigrating across an in vitro BBB model consisting of HCEC monolayer grown on porous artificial support dividing two media compartments have been isolated and proven to be targeting the brain in vivo. Due to their small size, selectivity of binding to brain endothelium and ability to cross the BBB, these antibody fragments are useful not only as vectors for the delivery of therapeutic and diagnostic agents into the brain, but also as molecular templates for designing drug and gene delivery vectors targeting the central nervous system.

Thus, according to one aspect, the present invention provides a process for enriching a phage display library of antigen-binding antibody fragments derived from llama antibodies with phage species binding selectively to human endothelial cells expressing BBB antigens, each antigen-binding fragment comprising at least a part of the variable heavy domain ($V_H$H or VH) of a llama antibody, said process comprising the steps of: (a) adsorbing the phage display library on first endothelial cells which do not express BBB antigens, (b) adsorbing phage species unbound to the first endothelial cells on second endothelial cells which express BBB antigens, and (c) stripping and recovering phage species bound to the second endothelial cells.

According to another aspect, the invention provides a process for the preparation of a human blood-brain barrier (BBB) transmigrating antibody fragment derived from a llama antibody, said process comprising the steps of: (a) providing a phage display library of antigen-binding antibody fragments derived from llama antibodies, (b) enriching the library for phage species selectively binding to endothelial cells expressing BBB antigens, (c) recovering from the enriched library phage particles selective to the endothelial cells expressing BBB antigens by comparing their binding to various endothelial cells from peripheral and brain tissues, (d) enriching the library for phage species internalized into the endothelial cells expressing BBB antigens, (e) identifying in the enriched libraries from steps (b) and (d) phage particles transmigrating across an in vitro BBB and recovering such phage particles, (f) comparing nucleotide sequences of DNA of phage particles recovered in steps (c) and (e) and selecting particles having both high selectivity to the endothelial cells expressing BBB antigens and transmigrating across the in vitro BBB, (g) amplifying DNA of the phage particles identified in step (f) and cloning into an expression vector a piece of DNA coding for the antibody fragments displayed by the phage particles, (h) transforming host cells with the expression vector, (i) incubating the transformed cells under conditions allowing the expression of the cloned piece of DNA, and (j) recovering the antigen-binding antibody fragment so prepared.

According to still another aspect, the invention provides an antibody fragment derived from a llama antibody, said fragment capable of transmigrating across the human blood-brain barrier (BBB) and selectively binding to an antigen on the surface of mammalian cells expressing BBB antigens.

According to yet another aspect, the invention provides a therapeutic or diagnostic agent, said agent comprising an antibody fragment derived from a llama antibody, said fragment capable of selectively binding to an antigen on the surface of mammalian cells expressing BBB antigens and transmigrating across the human blood-brain barrier (BBB), said antibody fragment being linked, directly or indirectly, covalently or non-covalently, to a therapeutic or diagnostic entity.

Other advantages, objects and features of the present invention will be readily apparent to those skilled in the art from the following detailed description of preferred embodiments in conjunction with the accompanying drawings and claims.

DETAILED DESCRIPTION OF THE PREFERRED EMBODIMENTS

In the following, positions of amino acid residues in antibodies and antibody fragments are indicated according to the Kabat numbering.

The present invention uses a large size (in the order of $10^9$) phage display library of single-domain fragments of variable heavy domains (VH and $V_HH$) of llama antibodies. The library, which has been generated using lymphocytes of a non-immunized animal (naïve library), can be used for in vitro selection against any antigen of interest as a target. The size of the library makes it highly probable that an antibody specific to the intended target will be identified among the library's sdAb fragments.

The choice of a naïve library as the source of llama antibodies was based in part on the fact that the immune system of camelids has evolved over time in harsh environments and that its unique physiological and morphological features have helped the camelids to withstand water scarcity, adapt to climate extremes and develop a natural resistance to deadly viral diseases. The sero-epidemiological studies have confirmed that camelids produce antibodies to a great number of pathogenic viruses without developing the disease (Werney et al., Infectious Diseases of Camelids, Blackwell's Wissenschaft Verlag, Berlin (1995)). This means that antibodies of therapeutic importance can be isolated from the antibody repertoire of camelids without prior immunization with potentially dangerous pathogens or fragments thereof.

Among the camelids, llama is the smallest animal which can survive in a severe, cold climate. Lymphocytes of a llama from a farm located in Osgoode (Canada) have been used to generate the phage display library of sdAbs of heavy chain antibodies. From this library, dAbs binding selectively binding to human cerebrovascular endothelial cells (HCEC) have been isolated. These sdAbs prove to target the brain in vivo and transmigrate the BBB.

Construction of a Naïve llama sdAb Phage Display Library

Figure 3:
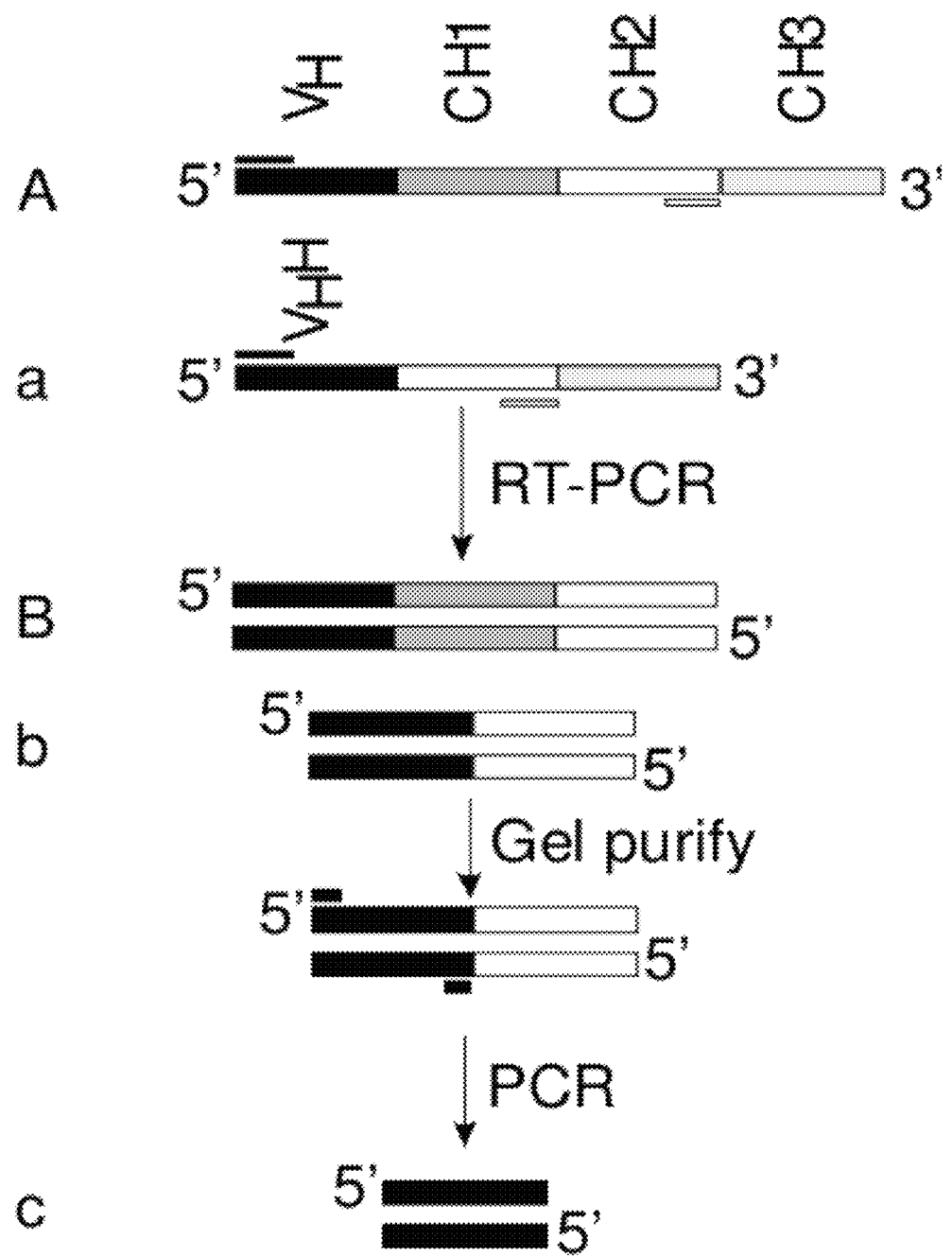
FIG. 3 is a schematic representation of steps involved in construction of the phage display library of llama sdAb antibody fragments according to the present invention. For simplicity, only the coding sequences of the mRNA transcripts are shown. A, a: heavy chain mRNA of conventional four-chain (A) and two-chain heavy chain (a) antibodies; B, b: RT-PCR product derived from A and a, respectively; c: $V_H$H derived from heavy chain antibodies. Variable heavy (VH and $V_H$H) and constant heavy (CH1) domains are marked with dark and light shading, respectively.

FIG. 3 depicts a schematic representation of steps involved in the construction of the $V_HH$-derived sdAb phage display library. As the first step, lymphocytes from the fresh blood of llama (from a farm located at Osgoode, Ontario, Canada) were prepared and their RNA was isolated using techniques well known to those skilled in the art. RT-PCRs (reverse transcriptase-polymerase chain reactions) were performed using primers annealing at the 5' end of VH or $V_HH$ and CH2 genes of IgG. The amplified products were separated and fragments of the expected size derived from conventional IgG (~900 bp) and heavy chain IgG (~600 bp) were observed on the agarose gel. The smaller fragment was gel purified and used in a second PCR to amplify the $V_HH$ genes. The amplification products were cloned into fd-tet (GIIID) vector, between the leader signal and gene III, to produce fusion proteins, which were displayed on the filamentous phage particles using a modified procedure.

As is well known to those skilled in the art, the probability of isolating a protein with high affinity or specificity against a target (antibody) of interest increases with the size of the library. Generally, two different types of vectors are used for generating phage display libraries: phagemid vectors and phage vectors. Libraries having size in the order of $10^8$ can be constructed with relative ease using phagemid vectors. However, a phagemid-based libraries suffers from some serious drawbacks. First, phagemid vectors provide typically a monovalent display and therefore may not select for lower binding (of lower affinity), but potentially important antibody fragments. Second, a phagemid-based library allows for the enrichment of phage particles displaying deleted versions of the antibody fragments. Such particles, often with no binding activity, are preferably selected during the panning process over those displaying the full-length fragments and therefore obscure the process of selection of the full-length binders. Third, constructing a phagemid-based library requires a helper phage and therefore library construction, panning and downstream phage binding assays become a far more complicated and tedious task. For these reasons the use a phage vector for the library construction is preferred.

One of the most widely used phage vectors is fd-tet (Zacher III et al., Gene, 9, 127-140 (1980)) which consists of fd-phage genome, plus a segment of Tn10 inserted near the phage genome origin of replication. Tn10 contains a tetracycline resistance gene, tetA, and thus confers tetracycline resistance to the host cells carrying the fd-tet vector. It has often been observed that the size of the fd-tet based library was generally low (in the range of $10^5$-$10^6$) (Harrison et al., Methods in Enzymology [Ed. Abelson, J. N.], 267, 83-109 (1996); Krebber et al., FEBS Letters, 377, 277-331 (1995)), possibly due to the toxic effect of tetA gene product on the host cells. According to the modified procedure of the present invention, the library was propagated as plaques in the absence of tetracycline, resulting in a llama $V_HH$ library of size of approximately $8.8 \times 10^8$. This is the largest size library ever obtained using fd-tet vector. Due to its size, the library has an enhanced probability of selecting therefrom proteins (antibody fragments) binding to almost any given target (antigen).

It would be known to those skilled in the art that, at least in principle, the display library of the invention could be generated using vectors other than phages, such as bacteria (e.g., *E. coli*) ([Daugherty, P. S., Olsen, M. J., Iverson, B. L., and Georgiou, G., 1999; Georgiou, G., Stathopoulos, C., Daugherty, P. S., Nayak, A. R., Iverson, B. L., and Curtiss, R., III, 1997])) or yeast (e.g., *Saccharomyces cerevisiae*) ([Kieke, M. C., Shusta, E. V., Boder, E. T., Teyton, L., Wittrup, K. D., and Kranz, D. M., 1999; Kieke, M. C., Cho, B. K., Boder, E. T., Kranz, D. M., and Wittrup, K. D., 1997; Cho, B. K., Kieke, M. C., Boder, E. T., Wittrup, K. D., and Kranz, D. M., 1998; Boder, E. T. and Wittrup, K. D., 1997])). Obtaining large libraries, comparable in size to phage display libraries, is, at least in theory, possible using these vectors. However, these display systems have not been of a widespread use, as they require expensive flow cytometry cell sorting instruments for selection. In addition, the *E. coli* display system is not suitable for panning against large macromolecules, such as proteins, due to the interference of the lipopolysaccharide layer of *E. coli* with the binding process ([Boder, E. T. and Wittrup, K. D., 1997]supra). Surface display of an scFv on mammalian cells has also been reported [Rode, H. J., Moebius, U., and Little, M., 1999]); [Rode, H. J., Little, M., Fuchs, P., Dorsam, H., Schooltink, H., de Ines, C., Dubel, S., and Breitling, F., 1996])). However, no antibody library has been so far constructed using vectors other than phages, as the construction and screening in these alternative display systems are not as rapid or versatile as for phage display libraries.

Sequence Analysis

Colony PCR of 80 randomly selected clones showed that more than 60% had the full-length $V_HH$ genes (sdAbs). The identity of the VL interface amino acids at position 44, 45 and 47 as well as the CDRs sequence of 28 randomly selected dAbs have been determined and are summarized in Table 1. Similarly to published results, the majority of the CDRs of the sequenced dAbs are 13-17 amino acid long, demonstrating that the llama sdAb library of the invention is derived from heavy chain antibodies. However, the present library is distinct in several aspects from the known $V_HH$ libraries.

Previously generated camelid sdAb libraries were characterized by typical presence of Glu, Arg and Gly in positions 44, 45 and 47, respectively, of the VL interface of $V_HH$ domain. The occurrence of cysteine at position 45 was also frequent in $V_HH$, as opposed to VH domain of four-chain IgGs. The present library, as shown by sequence analysis, lacks these characteristics, as only one sdAb (C35) has Glu44, Arg45 and Gly47. Five sdAbs (C1, C29, C43, C44, and C48) are characterized by Gly44, Leu45 and Trp47, the very same residues which are highly conserved in the VL interface of VH domain of conventional four-chain antibodies. The majority of sdAbs of the present library have Arg in position 45 of the VL interface. This occurrence of Arg45 is not unique to camelid $V_HH$, as a number of conventional antibodies, such as H1-I6 (VH) and V13 (VH), have been found to have Arg in position 45 (Blier et al., J. Immunol., 139, 3996-4006 (1987); Crews et al., Cell, 29, 59-66 (1981)). The presence of Gly at position 35 was observed to always accompany Phe at position 37, unlike a previously reported llama library in which this pairing was observed in only 50% of the sequences. This is noteworthy in view of the fact that Gly at position 35 results in local conformational changes that allow Trp101 to stack with Arg45 in addition to engaging in aromatic-aromatic interactions involving Phe37 and Trp 103. For the present library, 12 of 27 sdAbs have Trp at position 52a, whereas only 1 of the 51 previously published sequences have Trp at this position.

Another major difference between the present library and the previously reported $V_HH$ libraries of camelids concerns the CDR cysteins. Previously generated libraries were characterized by a high incidence of cysteine pairs in CDRs, whereas none of the 28 sdAbs (Table 1) of the present library had any cysteine in their CDRs. The library of the invention is therefore characterized by a very low presence or by the absence of cysteine residues in CDRs.

Finally, the present library, which was designed and constructed to contain only antibody fragments consisting of variable heavy chain domains ($V_HHs$), also contains a substantial number of typical conventional variable heavy domains (VHs) (for example, sdAbs C1, C29, C43, C44 and C48 of Table 1, some sdAbs of Table 2). This contamination is most likely the results of PCR cross-overs between the VHs and $V_HHs$ during the step of RT-PCR (FIG. 3) (Tomlinson et al., J. Mol. Biol., 227, 776-798 (1992); Muyldermans et al., Protein Eng., 7, 1129-1135 (1994)). These VHs are genuine antigen binding fragments, as shown in Table 2, produced in high yield in *Escherichia coli*. They are highly soluble, have excellent temperature stability profiles and do not display any aggregation tendencies (Tanha et al., manuscript in preparation; Vranken et al., submitted). The very close similarity of these molecules to human VHs makes them potentially very useful as therapeutic sdAbs.

For the library of the invention, amino acids of the VL interface are most frequently:
   at position 44-Gly, Glu, Gln, Lys, Ala and Asp,
   at position 45-Leu, Phe, Pro and Arg, and
   at position 47-Trp, Tyr, Phe, Leu, Ile, Val and Gly.

Selection of Antibody Fragments Binding Selectively to HCEC

1. Enrichment of Phage Displayed Llama Single-Domain Antibody (sdAb) Library for HCEC Specific Antibodies by Subtractive Panning Phage display libraries of peptides, proteins and antibodies have previously been used to identify 'binders' to biological targets in vitro and in vivo (Hoogenboom et al., Immunotechnology, 4, 1-20 (1998)), including purified antigens, whole cells and tissues.

Previous work using in vivo panning of phage displayed peptide library resulted in identification of organ specific peptide sequences in brain and liver (Pasqualini et al., Nature, 380, 364-366 (1996)). However, the brain targeting peptides were 'trapped' on the surface of blood capillaries and did not cross the BBB (Pasqualini et al., supra). Unlike peptides, antibodies are far more stable inside the cell and some antibodies have been shown to transmigrate the BBB via receptor-mediated transcytosis (Pardridge W. M., J. Cerebral Blood Flow. Metabol., 17, 713-731 (1997)). The antibodies according to the present invention are the smallest possible antigen binding antibody fragments that selectively bind to and transmigrate across human cerebromicrovascular endothelial cell (HCEC) monolayers and have properties of a brain delivery vector.

To select suitable fragments, inventors used the above-disclosed naïve llama sdAb phage displayed library derived from the $V_HH$ of the heavy chain IgGs which occur naturally in the absence of light chain (Muyldermans et al., J. Mol. Recog., 12, 131-140 (1999)). The average molecular weight of these sdAbs is 13 kDa, approximately half the size of a scFv. As discussed above, the library (about $8.8 \times 10^8$ species) exists in a filamentous phage vector and is propagated as plaques in the absence of antibiotics. Characterization of more than a dozen sdAbs isolated from this library has shown $K_d$s in the low micromolar range (data not shown). Two features of this library are of particular importance for isolating antibodies with the ability to penetrate and/or transmigrate cell layers. First, the library is constructed using a phage vector, as opposed to a phagemid vector, and therefore the display of sdAbs is multivalent. The sdAbs in the multivalent presentation mode favor receptor cross-linking and phage internalization (Becerril et al., Biochem. Biophys. Res. Commun., 255, 386-393 (1999)) and are more effective in capturing and retaining 'binders' during the course of panning. The affinity of such sdAbs can easily be improved by mutagenesis because they are derived from a naïve repertoire and have not gone through in vivo affinity maturation. The second important feature of this library is the small size of sdAbs (~13 kDa as compared to 150 kDa for an IgG), a preferred choice for macromolecules required to penetrate dense tissues such as the BBB (Muyldermans et al., supra).

Figure 4:
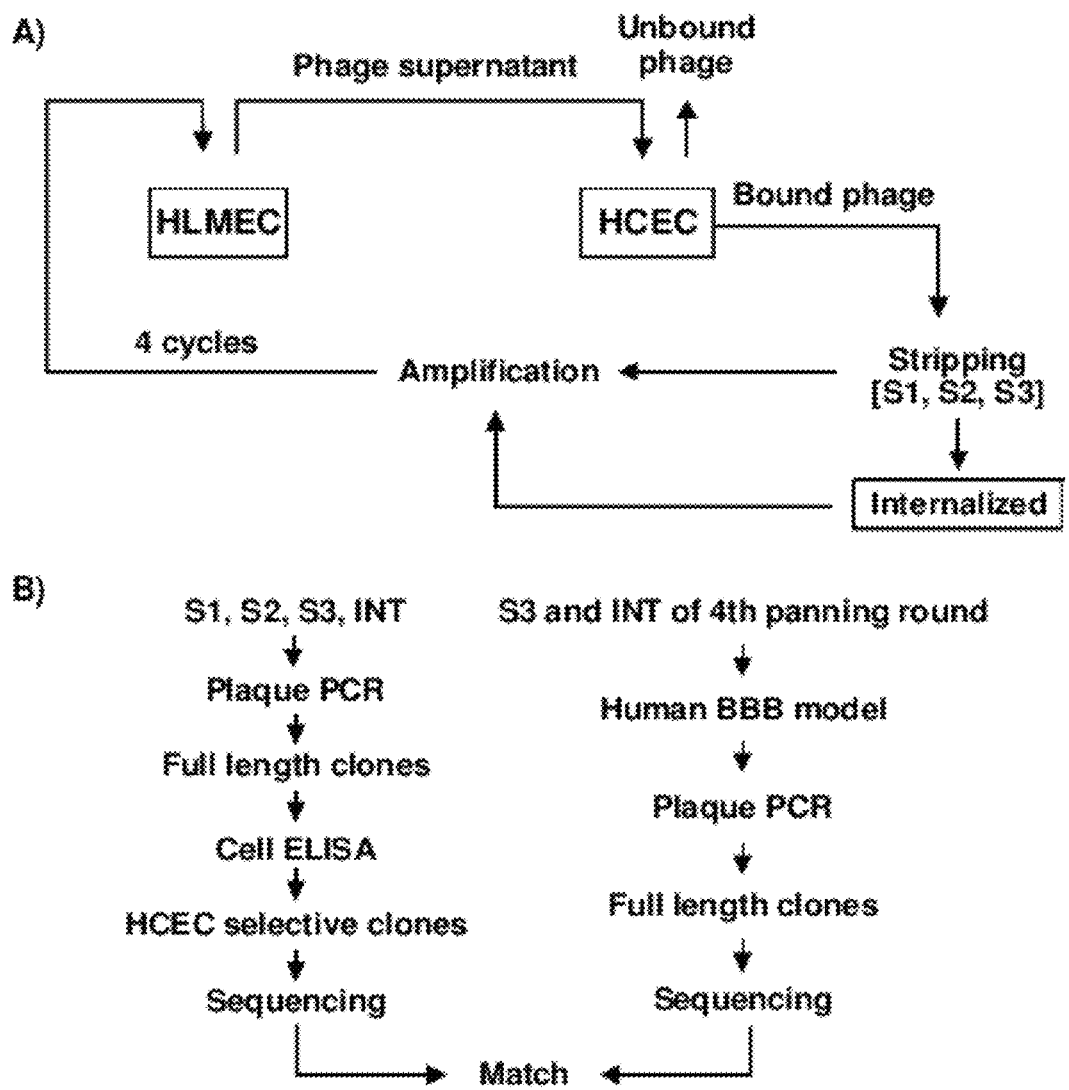
FIG. 4 is a schematic representation of steps involved in selection of blood-brain barrier-binding sdAbs from llama sdAb phage-displayed library. A) Subtractive panning protocol of llama single-domain antibody phage-displayed library against human lung microvascular cells (HLMEC) and human cerebromicrovascular endothelial cells (HCEC) used. Clones that bound selectively to HCEC were recovered by three stripping washes, and those internalized by HCEC were recovered by cell lysis. Phage recovered from S3 and internalized fractions were amplified and used as input library for each subsequent round of panning Total of four panning rounds was performed. B) Functional selection of phage clones from the enriched library was done based on two criteria: a) selectivity and high affinity binding to HCEC (left branch), determined by phage binding to HCEC and peripheral endothelial cells by phage ELISA, and b) the ability of phage clones to transmigrate across in vitro BBB model (right branch). Only phage clones with full $V_HH$ inserts fulfilling both functional criteria were chosen for further characterization.

The subtractive panning used to enrich for BBB-specific sdAbs from the naïve phage displayed library is schematically shown in FIG. 4, part A. Two endothelial cell types were used for subtractive selection: human lung microvascular endothelial cells (HLMEC) and human cerebromicrovascular endothelial cells (HCEC). It was previously shown that HCEC express BBB-specific antigens (e.g., γ-glutamyl transpeptidase, P-glycoprotein, HT7, occludin, etc.) that are not expressed in peripheral endothelial cells, including HLMEC (Stanimirovic et al., J. Cell Physiol., 169, 455-467 (1996)).

In order to identify BBB-selective sdAbs, the naïve phage library was preabsorbed onto HLMEC to remove non-specific, common endothelial binders, and then applied to HCEC. After removing unbound phage, phage bound to HCEC was dislodged by three rounds of highly stringent stripping washes (S1, S2 and S3) to favor the selection of sdAbs with higher affinity. HCEC were then lysed to capture the internalized phage (Int). PCR on 80 individual plaques from 51, S2, S3 and Int fraction revealed that the output phages from S3 contained the highest percent of clones with the full-length $V_HH$ insert. The phage in S3 fraction was then amplified and used as an input phage for second round of panning Four rounds of panning were performed and for each round the input phage was derived from the fraction which showed the highest percent of phage with full-length $V_HH$ insert.

The progress of panning was monitored by phage titer measurements, PCR and phage ELISA. As shown in Table 2, the phage titers bound to the HLMEC cells decreased with each subsequent round of panning while those bound to HCEC dropped after the first round and then progressively increased from the second to fourth round of panning, indicating enrichment for HCEC-specific sdAbs. After fourth round of panning, fractions 51, S2, S3 and Int contained 80%, 80%, 70% and 30%, respectively, of clones with the full-length $V_HH$ insert. The remaining clones either had no inserts or possessed one or two of the CDR domains and framework regions.

TABLE 2

Phage titers determined after various steps of subtractive panning procedure.

| Panning Rounds | 1 | 2 | 3 | 4 |
|---|---|---|---|---|
| Phage bound to HLMEC | $6.0 \times 10^{11}$ | $1.9 \times 10^{11}$ | $0.6 \times 10^{11}$ | $0.08 \times 0^{11}$ |
| Phage applied onto HCEC | $4.0 \times 10^{11}$ | $8.1 \times 10^{11}$ | $9.4 \times 10^{11}$ | $9.92 \times 10^{11}$ |
| Phage bound to HCEC | | | | |
| Strip 1 | $2.1 \times 10^8$ | $1.3 \times 10^7$ | $1.3 \times 10^7$ | $1.5 \times 10^7$ |
| Strip 2 | $0.2 \times 10^7$ | $0.9 \times 10^7$ | $1.1 \times 10^7$ | $1.9 \times 10^7$ |
| Strip 3 | $0.9 \times 10^6$ | $0.9 \times 10^6$ | $4.4 \times 10^7$ | $4.4 \times 10^7$ |
| HCEC cell lysate (internalized) | $0.7 \times 10^7$ | $0.1 \times 10^7$ | $4.2 \times 10^7$ | $9.9 \times 10^7$ |

Figure 1:
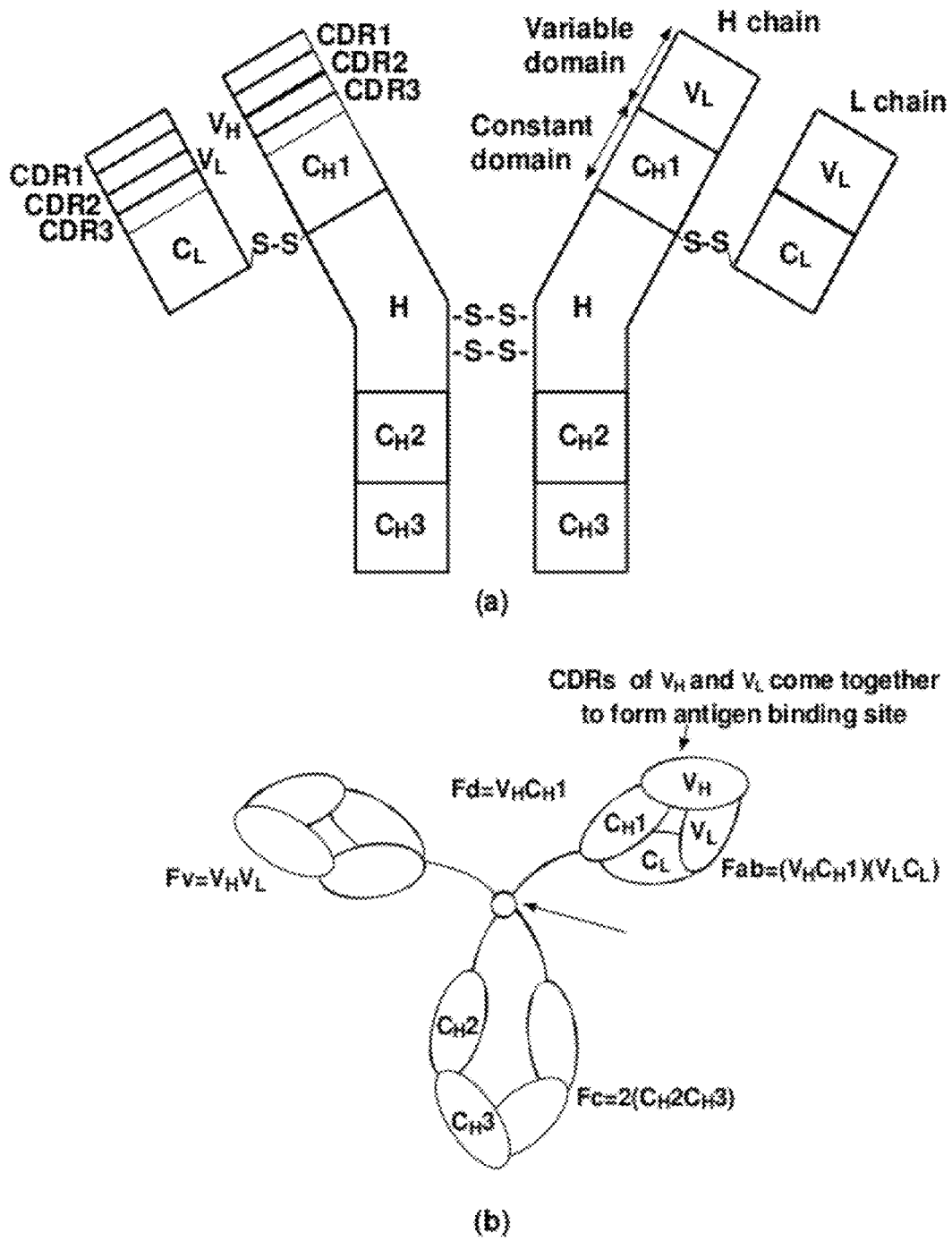
FIG. 1 is a schematic representation of a typical four-chain IgG-type immunoglobulin (antibody) showing (a) the structure and arrangement of heavy and light chains and the approximate positioning of interchain disulfide bonds, and (b) the organization of the antibody molecule into paired domains.
Figure 2:
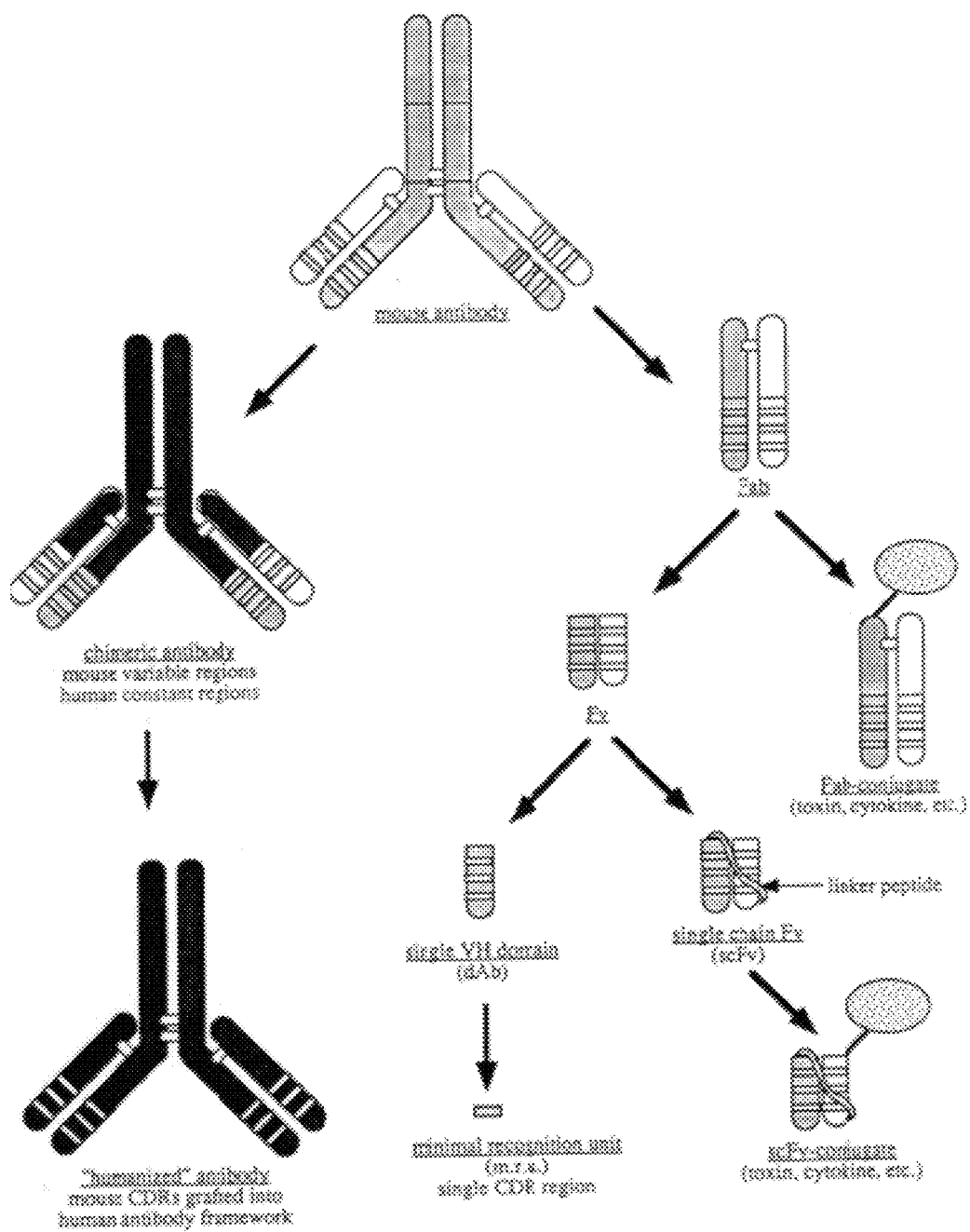
FIG. 2 is a schematic representation of various modifications and fragments of IgG-type antibodies, and antigen-binding fusion proteins derived from such fragments.

$10^{12}$ phage was preabsorbed onto HLMEC and unbound phage was then applied to HCEC. Bound phage was dislodged by three stripping washes. Internalized phage was harvested by cell lysis. Second and third rounds of panning were started with $10^{12}$ of amplified phage from strip 3 of the previous panning. The fourth round of panning was started with $10^{12}$ of amplified phage from strip 1 of the third panning 2. Selection of Candidate sdAbs from the Enriched Llama sdAbs Phage Displayed Library Based on Functional Criteria Further selection of sdAb species from the library enriched for HCEC specific binders obtained by subtractive panning was done using two functional criteria: i) selective binding to HCEC compared to peripheral endothelial cells, and ii) the ability of phage clones to transmigrate across in vitro BBB model (FIG. 1, part B).

2.1. Selection for Specificity and Higher Affinity by Phage ELISA

Figure 5:
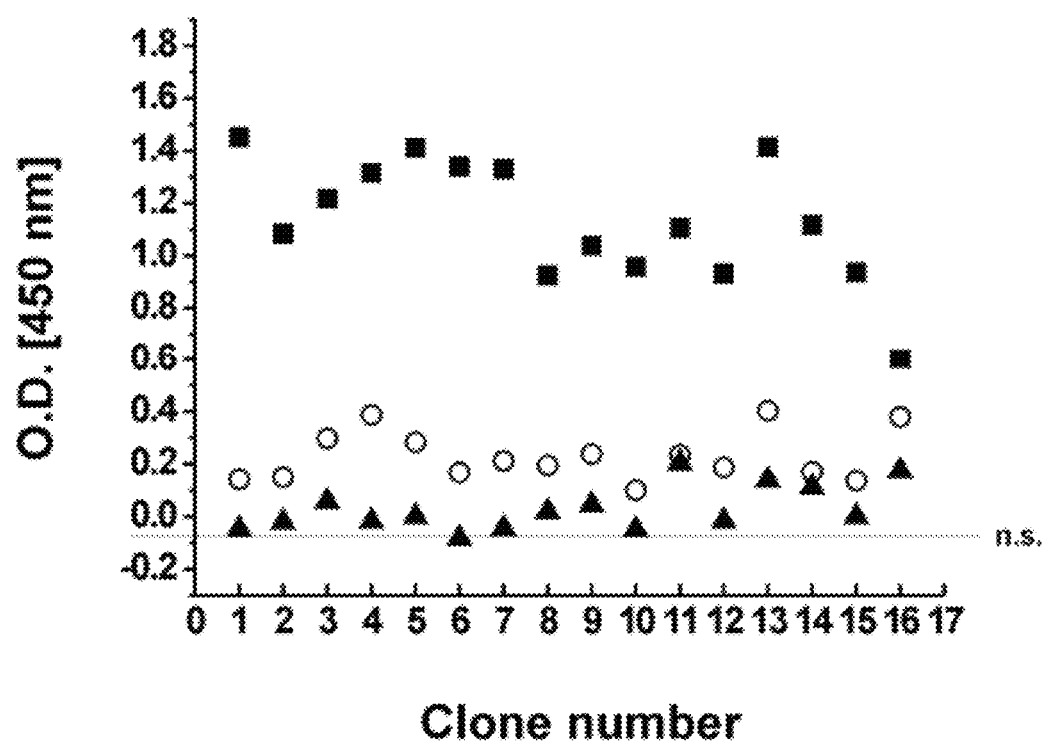
FIG. 5 is a graph showing binding of selected phage-displayed sdAb clones to endothelial cells. Relative binding affinity of 16 phage clones with full-length $V_HH$ inserts to HCEC (black squares), HLMEC (black triangles), and HUVEC (open circles) was determined by ELISA against phage coat protein P8. Cells grown in 96-well plates were exposed to the same amount of each phage clone for 1 h, and after washing the bound phage was detected by ELISA. The absorbance values were normalized for non-specific binding (n.s.).

Following 4 rounds of subtractive panning, 58 clones with full-length $V_HH$ inserts were identified by plaque PCR. Phage ELISA using all 58 clones revealed that 16 clones repeatedly showed a selective binding to HCEC as compared to HLMEC or human umbilical vein endothelial cells (HUVEC) (FIG. 5).

Sixteen clones that selectively bound HCEC identified by phage ELISA were subsequently sequenced and found to contain three different sequences (Table 3). Two sequences differed only at position 34 in CDR1 (Ile to Met) (Table 3) indicating that all 16 clones belong to only 2 sdAb species (Table 3), designated FC5 and FC44. These two sdAbs have 4 amino acids, Phe, Glu, Arg and Phe at positions 37, 44, 45 and 47 which are signature residues for llama $V_HHs$ (Muyldermans et al., supra). Both sdAbs are characterized by a 17 residue CDR2 and the absence of additional Cys at positions 30-33 or 45, hence, belonging to subfamily 1a (Nguyen et al., EMBO J. 19, 921-930 (2000)). FC5 and FC44 showed no significant homology to each other in their CDRs suggesting that they recognize different antigenic epitopes.

2.2. Selection of sdAbs with Ability to Transmigrate In Vitro BBB Model

Figure 6:
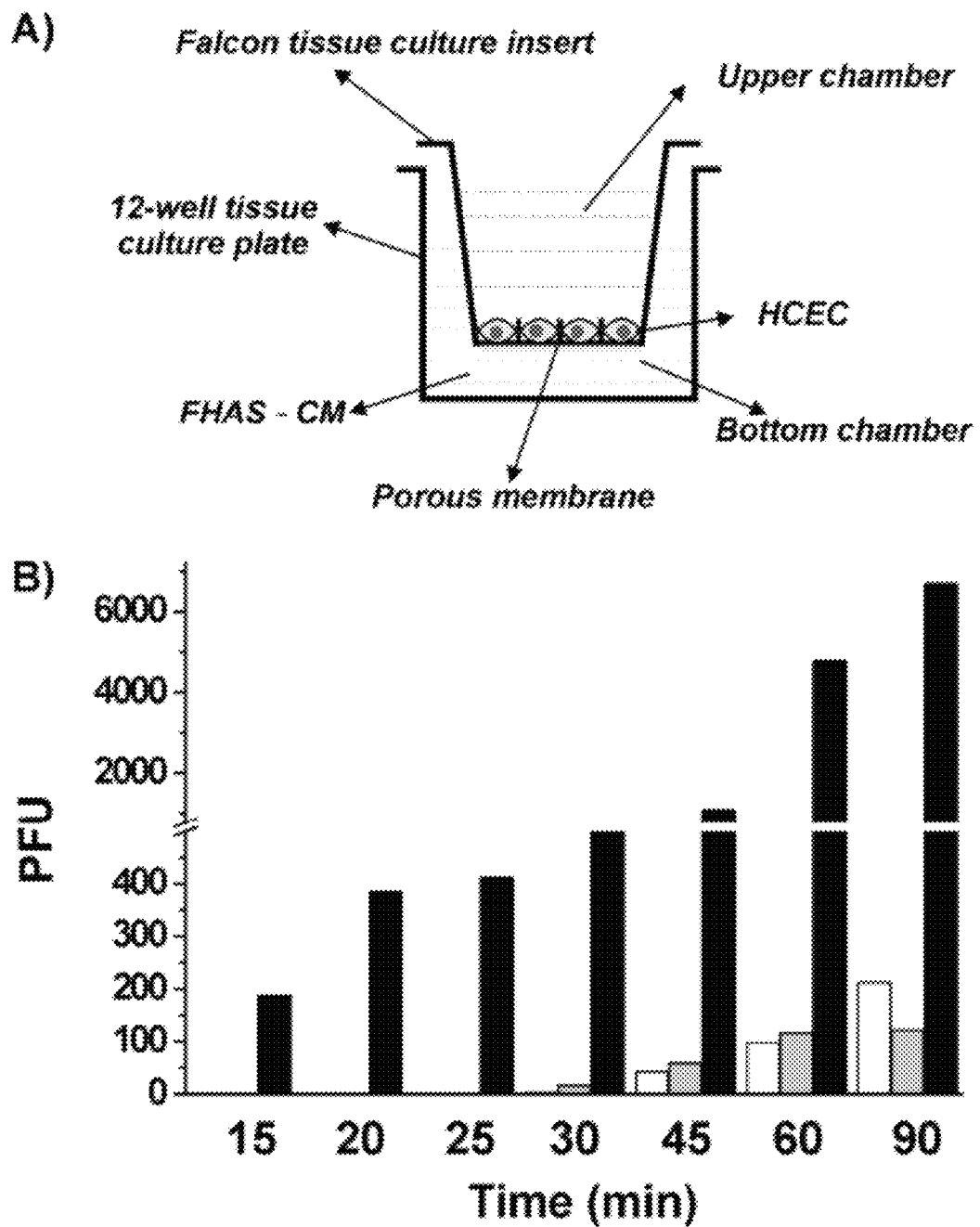
FIG. 6 is a schematic and a graph showing the in vitro BBB model used and transmigration of enriched llama sdAb phage-displayed library across the in vitro BBB model. A) In vitro BBB model consists of human cerebromicrovascular endothelial cells (HCEC) grown as a monolayer on a semipermeable membrane of the tissue culture insert. HCEC are exposed to media conditioned by fetal human astrocytes (FHAS-CM) applied to the bottom compartment. To estimate transcellular passage, phage was added to the upper chamber and aliquots from the bottom chamber were collected over various periods of time. B) $10^{11}$ transducing phage units of the wild type phage (open bars), phage displaying an unrelated sdAb (NC11) (grey bars), and phage library enriched for high affinity HCEC binding and HCEC internalizing phage (black bars) were applied to the top chamber of triplicate BBB assemblies and the phage titre was determined in aliquots of the bottom chamber at the indicated time points.

A separate round of selection was performed to select species capable of crossing in vitro BBB model (FIG. 4, part B). In vitro BBB model used for these studies consisted of a HCEC monolayer grown on a semi-permeable membrane positioned to separate two media compartments as shown in FIG. 6, part A. Media conditioned by fetal human astrocytes (FHAs) were used to induce the BBB phenotype of HCEC. The model has been characterized in detail previously (Murugananandam et al., FASEB J., 13, 1187-1197 (1997)). Similar in vitro BBB models using bovine (Dehouck et al., J. Neurochem., 58, 1790-1797 (1992); Pardridge et al., J. Pharmacol. Exp. Therap., 253, 884-891 (1990)) or porcine (Franke et al., Brain Res., 816, 65-71 (1999)) cerebral endothelial cells have been used to predict brain bio-availability of variety of compounds with different physico-chemical properties, including those transported across the BBB by energy-dependent mechanism(s).

Phage contained in the third stripping wash and internalized fractions of the fourth panning round was amplified and $10^{11}$ pfu was applied to the top chamber of the in vitro BBB model. Phage titers in the bottom chamber were determined after various time intervals. The integrity and tightness of HCEC monolayers were assessed by the diffusion of the

TABLE 3

Sequences of phage-displayed sdAbs clones that transmigrated across the human in vitro blood brain barrier model

```
            1                   10                  20                          30
FC5     E V Q L Q A S G G G L V Q A G G S L R L S C A A S G F K I T H Y T M
FC44    E V Q L Q A S G G G L V Q A G G G L R L S C S A S V R T F S I Y A M
FC7     E V Q L Q A S G G G L V Q A G G G L R L S C S A S V R T F S I Y A I 40                  50      a           60
FC5     G W F R Q A P G K E R E F V S R I T W G G D N T F Y S N S V K G R F
FC44    G W F R Q A P G K E R E F V A G I N R S G D V T K Y A D F V K G R F
FC7     G W F R Q A P G K E R E F V A G I N R S G D V T K Y A D F V K G R F 70                  80    a b c             90
FC5     T I S R D N A K N T V Y L Q M N S L K P E D T A D Y Y C A A G S T S
FC44    S I S R D N A K N M V Y L Q M N S L K P E D T A L Y Y C A A T W A Y
FC7     S I S R D N A K N M V Y L Q M N S L K P E D T A L Y Y C A A T W A Y 100a b c d e f g h                  113
FC5     T A T P L R V - - - D Y W G K G T Q V T V S S       SEQ ID NO: 85
FC44    D T V G A L T S G Y N F W G Q G T Q V T V S S       SEQ ID NO: 86
FC7     D T V G A L T S G Y N F W G Q G T Q V T V S S       SEQ ID NO: 87
``` small paracellular marker, sodium fluorescein (Muruganandam et al., supra). The permeability coefficient ($P_e$) for sodium fluorescein was $[(3.2\pm0.3)\times10^{-3}]$cm/min, whereas HCEC monolayers were virtually impermeable for 70 kDa dextran (data not shown).

Both the wild type (i.e., empty) phage and the phage library displaying unrelated antibody (NC11) produced low phage titers in the bottom chamber 60-90 min after addition to the top compartment (FIG. 6, part B). In contrast, the amplified library enriched for HCEC binding and internalized phage clones produced high titers in the bottom chamber as early as 15 min after addition, and titers reached 5000-7000 pfu at 60-90 min (FIG. 6, part B). Empty membrane did not restrict the passage of phage particles, as the titers in the bottom chamber were 15-40×10$^4$ pfu after 60-90 min of diffusion (data not shown). Plaque PCR of phage clones that had transmigrated across the in vitro BBB model between 15-30 min showed full-length (600 bp) V$_H$H inserts in 10% of all clones. Sequencing revealed that all phage clones with the full-length inserts contained FC5 or FC44 gene sequences. Plaque PCR and sequencing of full-length clones applied to the top chamber showed that this fraction, in addition to FC5 and FC44, contained clones with various other sequences.

Given the molecular weight (~1.4×10$^4$ kDa), the dimensions of filamentous phage particles (9×900 nm), and the complete barrier that HCEC monolayers presented for high molecular weight dextran, it was concluded that phage crossed the HCEC monolayer using a transcellular route. The transcellular phage transport was greatly facilitated by enriching phage library for species that confer tropism for HCEC binding and internalization. The mechanism by which phage enters mammalian cells and crosses cellular barrier(s) are poorly understood. Filamentous bacteriophage expressing the antibody against the growth factor receptor ErbB$_2$ has been shown to enter mammalian cells and express the reporter gene inserted in the phage genome (Poul et al., J. Mol. Biol., 288, 203-211 (1999)). It has been suggested that filamentous bacteriophage enters mammalian cells via receptor-mediated endocytosis (Becerril, et al., supra, Poul, et al., supra) and research addressing viral infections of the brain has demonstrated the ability of viral particles to transmigrate across the intact BBB (Banks et al., J. Cell. Sci., 11, 533-40 (1998)).

3. Functional Characterization of FC5- and FC44-c-myc-His$_5$ Fusion Proteins (His$_5$ Shown in SEQ ID NO: 101)

To assess functional properties, fusion proteins of FC5, FC44, and an unrelated anti-idiotypic antibody derived from the llama library (NC11; used as a negative control) with c-myc and His$_5$ tags (SEQ ID NO: 101) were expressed in a bacterial expression system and purified. His$_5$ tag (SEQ ID NO: 101) was used for the affinity purification on a Ni$^{2+}$ column, and for immobilization of fusion proteins on a Ni$^{2+}$-coated ELISA plate. C-myc tag was used to detect the sdAbs by ELISA and/or immunocytochemistry using HRP-conjugated anti-c-myc antibodies. Molecular weight of these fusion proteins was ~16 kD.

3.1. Binding and Uptake of Fusion Proteins in Endothelial Cells

Figure 7:
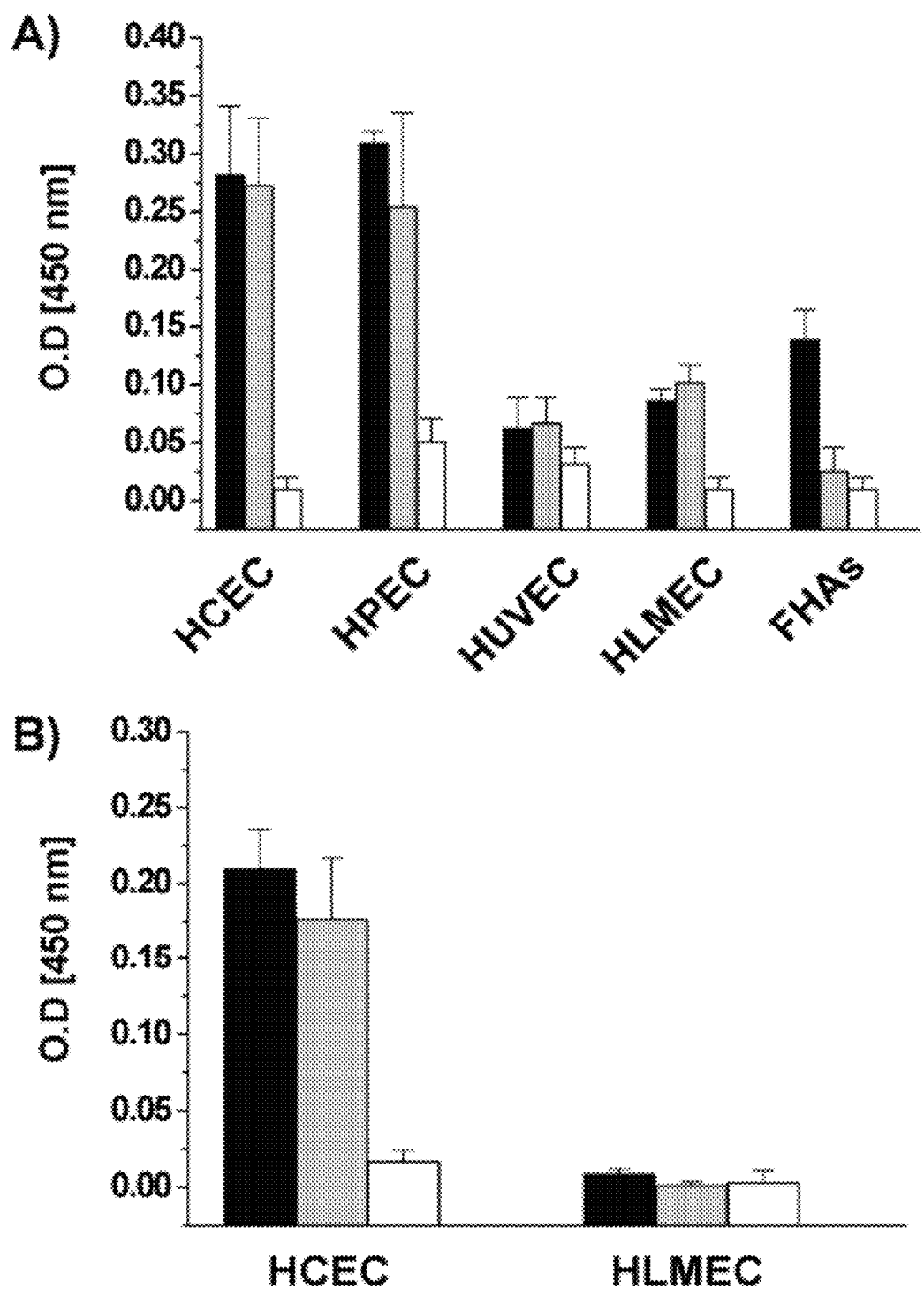
FIG. 7 is a graph showing the binding of sdAb fusion proteins to endothelial cells. Binding of FC44 (black bars), FC5 (grey bars), and NC11 (open bars)-c-myc-His$_5$ (His$_5$ shown in SEQ ID NO: 101) fusion proteins to (A) cell lysates of human cerebromicrovascular endothelial cells (HCEC), human pial artery endothelial cells (HPEC), human umbilical vein endothelial cells (HUVEC), human lung microvascular endothelial cells (HLMEC), and fetal human astrocytes (FHAs), and (B) to live HCEC and HLMEC. The binding was determined by ELISA against c-myc. Each bar represents the mean±S.E.M. of 6 wells in one representative experiment out of three independent experiments.

Binding of the purified sdAbs to cell lysates of various endothelial cells derived from brain or peripheral organs, including HCEC, human pial artery endothelial cells (HPEC), HLMEC, HUVEC, and fetal human astrocytes (FHAs) demonstrated a selective binding of FC5 and FC44 to endothelial cells derived from the brain vasculature (i.e., HCEC and HPEC) (FIG. 7, part A). FC44 also bound to FHAs lysates (FIG. 7, part A), suggesting that antigen 'receptors' for this antibody may be expressed in brain cells other than endothelium. Binding of NC11 was at the background level. FC5 and FC44 also demonstrated a selective binding to live HCEC compared to HLMEC (FIG. 7, part B), while NC11 failed to bind either cell type.

Figure 8:
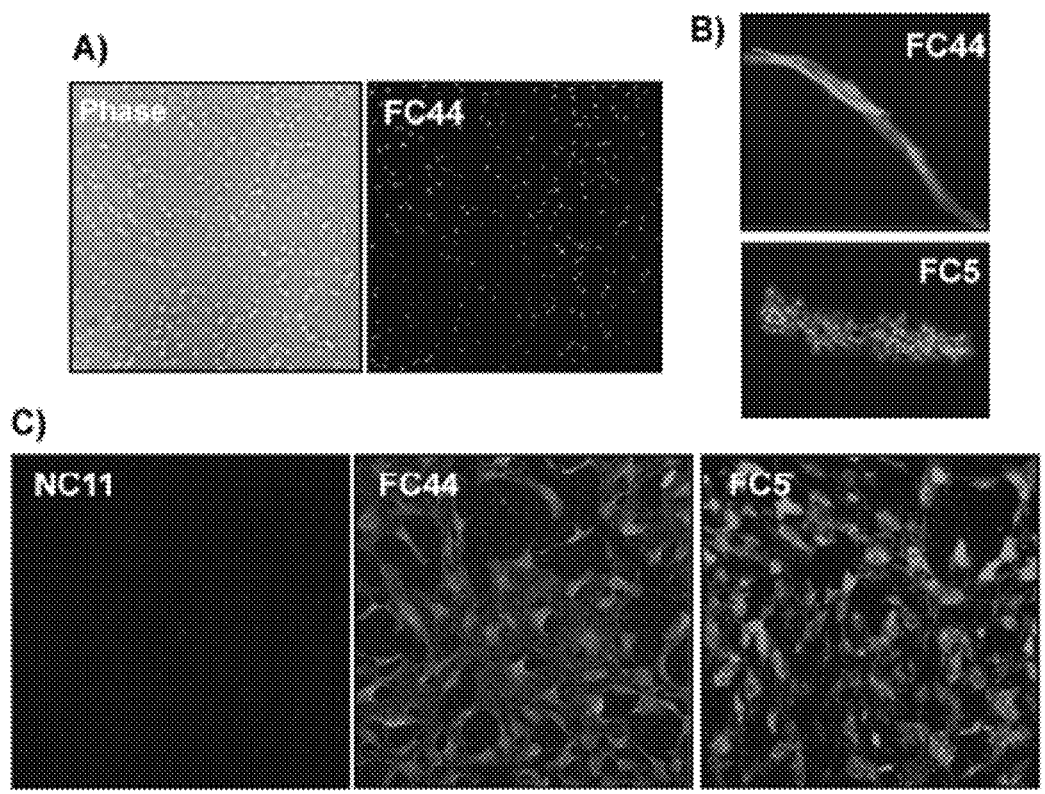
FIG. 8 is a photograph illustrating the binding of sdAb fusion proteins to brain endothelial cell fractions and uptake into brain endothelial cell. The antibodies were labeled with Alexafluor 488/532 and applied to vesicular or membrane fractions or to live cells for 2 h. After washing to remove unbound antibodies, fluorescence bound to cellular fractions or taken up by cells was detected using confocal or fluorescence microscopy. Panels show binding of the fluorescently labeled FC44, FC5, and NC11 c-myc-His$_5$ (His$_5$ shown in SEQ ID NO: 101) fusion proteins to (A) endocytic vesicles and (B) membranes isolated from human cerebromicrovascular endothelial cells (HCEC), and (C) the uptake of these antibodies into live HCEC.

FC5 and FC44 labeled with the fluorescent dye, Alexafluor 488, bound to both the vesicular (FIG. 8, part A) and membrane (FIG. 8, part B) fractions of HCEC. Furthermore, fluorescently labeled FC5 and FC44, but not NC11, were taken up by live HCEC (FIG. 8, part C). No cellular toxicity of either sdAb was observed over 24 h period at 30 µg/ml (data not shown). Under the same experimental conditions, no uptake of FC5 and FC44 was detected in HLMEC (data not shown).

The uptake of FC5 and FC44 into HCEC was significantly reduced at 22° C., and completely abolished at 4° C. (data not shown), while the uptake of lipid-soluble diazepam was unaffected by temperature, suggesting that FC5 and FC44 are most likely internalized into HCEC by an energy-dependent pathway. The receptor-mediated endocytosis of transferrin/transferrin receptor complex has also been shown to be strongly suppressed by hypothermia and/or energy deprivation (Tsuji et al., Adv. Drug Delivery Rev., 36, 277-298 (1999); Moos et al., Cell. Mol. Neurobiol., 20, 77-95 (2000)).

3.2. Transmigration of Fusion Proteins Across in Vitro BBB Model

Figure 9:
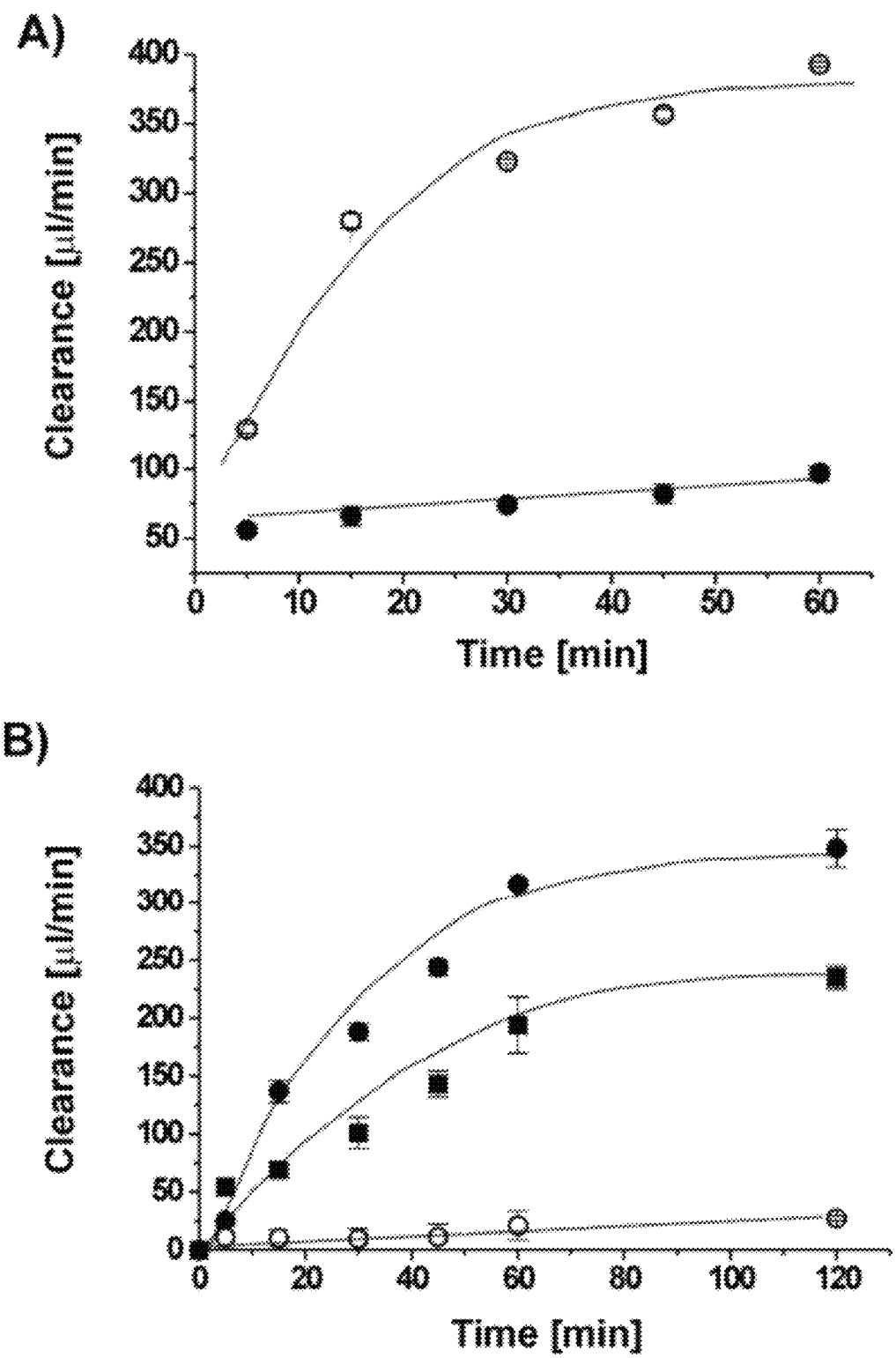
FIG. 9 is a graph showing the transmigration of sdAb fusion proteins across the in vitro blood-brain barrier model. Panels show clearances of (A) 10 kDa radiolabeled dextran and (B) FC5, FC44, and NC11 c-myc-His$_5$ (His$_5$ shown in SEQ ID NO: 101) fusion sdAbs across the in vitro human BBB model. A) 10 kDa dextran was added to the top chamber and fluorescence intensity was determined in aliquots collected from the bottom chambers of triplicate empty membranes (open circles) and membranes covered by HCEC monolayers (closed circles) at the indicated time points. B) 100 μg of FC5 (gray circles), FC44 (black circles), or NC11 (open circles) was added to the top chamber of the BBB model, and concentrations of the antibodies in aliquots collected from bottom chambers at the indicated time points were determined using a nickel-trap ELISA. Clearance values were determined as described. Each point represents the mean±S.E.M. of clearance values of 3 membranes in one representative experiment out of three independent experiments.

The ability of FC5 and FC44 fusion proteins to transmigrate across the HCEC monolayers was investigated using in vitro BBB model described. The concentration of the sdAbs in the bottom chamber at given times was determined using a nickel-plate ELISA, and clearance values calculated as described (Muruganandam et al., supra). The HCEC monolayer was found to be virtually impermeable for 10 kD dextran (FIG. 9, part A) and for NC11 fusion protein (FIG. 9, part B). In contrast, both FC5 and FC44 fusion proteins crossed HCEC monolayer (FIG. 9, part B) showing clearance values comparable to those seen across empty membranes (2.28±0.27 vs. 2.42±0.15 µl/min for FC5, respectively; 3.23±0.62 vs. 2.51±0.21 µl/min for FC44, respectively; 0.097±0.005 vs. 2.33±0.27 µl/min for NC11, respectively). The clearance for both FC5 and FC44 was linear over 60 min (FIG. 9, part B) with the clearance of FC44 slightly higher than that of FC5 (FIG. 9, part B). FC5, FC44, or NC11 did not change in vitro BBB permeability as assessed by clearance of sodium fluorescein and measurements of the transendothelial electrical resistance. Thus, FC5 and FC44 fusion proteins retained the ability to transmigrate across the in vitro BBB model, carrying across an intact c-myc-His$_5$ (His$_5$ shown in SEQ ID NO: 101) peptide tag.

4. In Vivo Brain Homing of FC5 and FC44

To assess the ability of FC5 and FC44 to target brain in vivo, both phage-displayed FC5 and FC44 and soluble FC5 and FC44 fusion proteins were injected intravenously (i.v.) into mice, and the biodistribution in various organs was analyzed after 4-6 hours using phage titre determination and Western blot detection, respectively.

Figure 10:
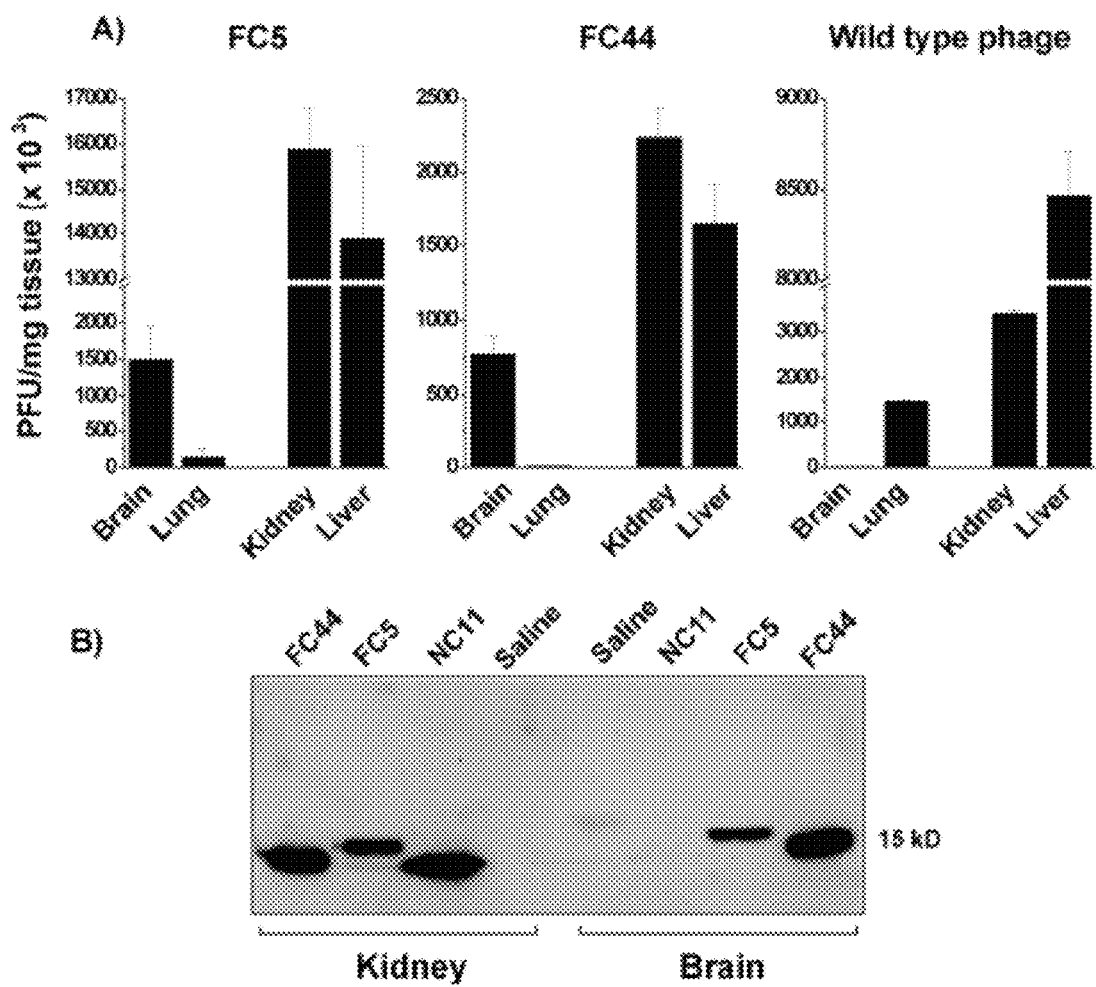
FIG. 10 is a graph and a photograph showing the biodistribution of llama sdAb libraries and selected sdAb fusion proteins in mice. A) In vivo distribution of phage in various organs of mice injected with $10^9$ transducing phage units of the wild type phage and phage carrying FC5, or FC44 sdAb. The mice were perfused transcardialy 4 hours after the phage injection, and phage titers in the brain, lung, kidney and liver were determined. Each bar is the mean±S.D. of phage titres determined from 3 animals. B) Biodistribution of the FC5, FC44, and NC11-c-myc-His$_5$ (His$_5$ shown in SEQ ID NO: 101) fusion proteins in various organs of mice after i.v. injection of 30 μg/kg of respective sdAbs. The organs were harvested 4 h after injection and sdAbs were extracted by affinity purification on a Ni$^{2+}$ column and detected by immunoblot against c-myc tag. The blot is representative of the results obtained from 3 animals.

Both phage-displayed FC44 and FC5 (FIG. 10, part A) produced significantly higher titers in the brain tissue than in the lung tissue, whereas wild type phage library produced no measurable titers in the brain and significant titers in the lung (FIG. 10, part A). Kidney and liver tissues produced high phage titers for FC44, FC5 and wild type phage libraries (FIG. 10, part A), suggesting that these organs are likely elimination/excretion routes for phage particles.

FC5, FC44, and NC11 fusion proteins were extracted from perfused mouse tissues 4-6 h after injection, using affinity purification on a Ni$^{2+}$ column, and were detected on a Western blot using an anti-c-myc antibody (FIG. 10, part B). Both FC5 and FC44 fusion proteins, but not NC11 fusion protein, were detected in the brain tissue (FIG. 10, part B) after capillary depletion, as well as in the brain capillary fraction (data not shown). Kidney tissue showed strong bands for all three sdAb fusion proteins (FIG. 10, part B).

These results show that FC5 and FC44 sdAbs derived by in vitro subtractive panning and functional selection procedures have the ability to target the brain after i.v. injection in vivo, in a partly selective manner. These results also prove that small peptides can be attached to and transported along with FC5 and FC44 as a fusion protein(s) (MW of c-myc-His$_5$, tag (His$_5$ shown in SEQ ID NO: 101) ~3 kD; 26 amino acids) across the BBB in vitro and in vivo.

From the above, it would be obvious to those skilled in the art that antibody fragments of the present invention can be used as carriers (vectors) for therapeutic and diagnostic agents to be specifically delivered to the surface and/or the interior of the cerebral endothelial cells and/or across the blood-brain barrier. Such therapeutic or diagnostic agents include hydrophilic molecules, peptides, proteins, pieces of DNA, fluorescently or radioactively labelled compounds, phage particles, liposome formulations, polymer formulations etc. Such agents can be attached to the antibody fragments either directly or indirectly (e.g., via suitable linkers), either by covalent or non-covalent bonds, for example by using complementary pieces of DNA attached to the antibody fragment and the molecule of a therapeutic or diagnostic agent.

5. HCEC Antigen(s) Recognized by FC5 and FC44

Figure 11:
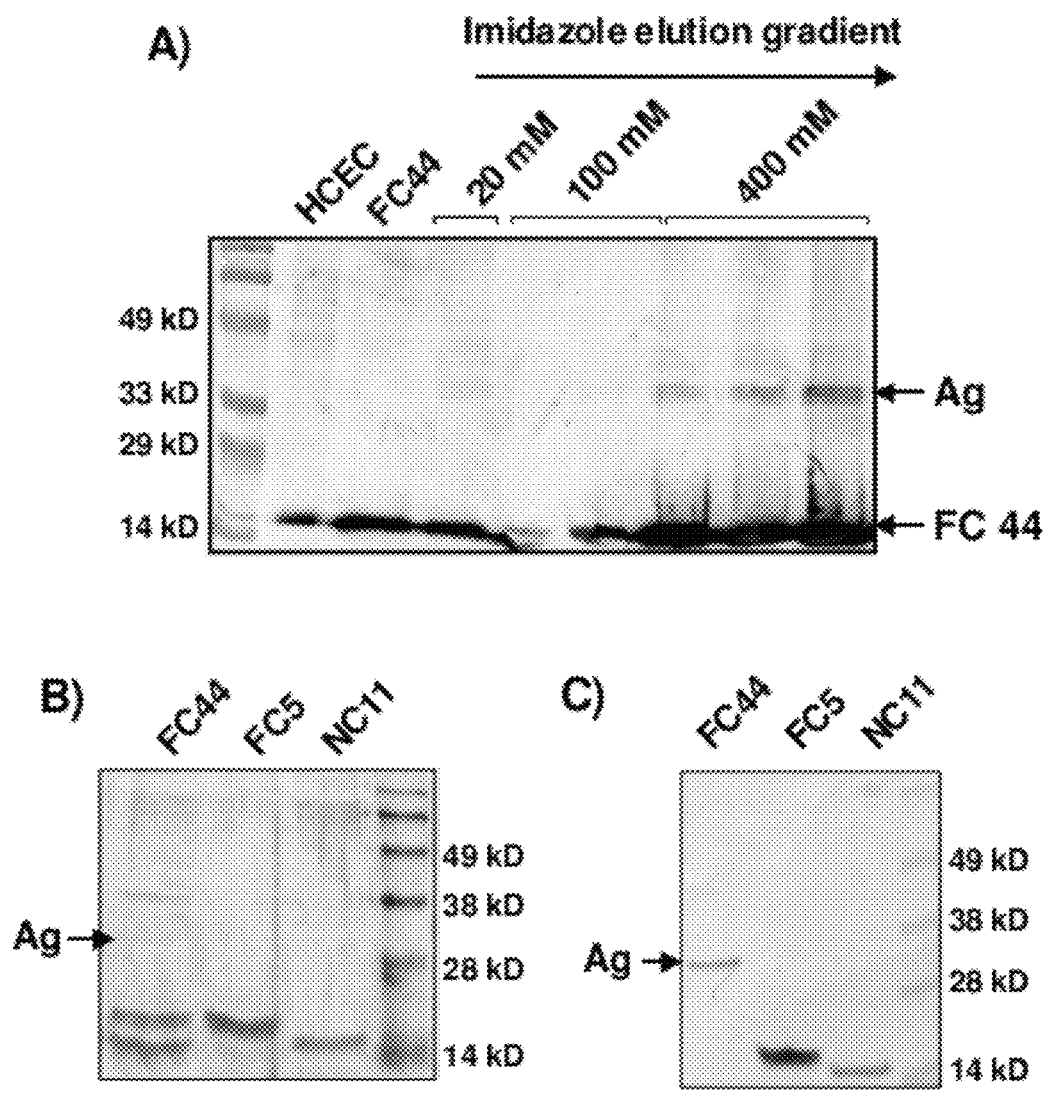
FIG. 11 is a photograph showing the affinity purification of the antigen/sdAb complex from HCEC. A) A gradient elution of the antigen/antibody complex with increasing strengths of imidazole buffer. Denatured FC44/antigen complex was resolved on 12% SDS-PAGE, transferred to nitrocellulose membrane, and antigen was detected by probing the membrane with FC44 fusion protein and subsequently with anti-c-myc antibody as described in the Experimental Procedures. B) Silver stained gel of respective resolved FC44, FC5, and NC11 antigens eluted from the Ni$^{2+}$ affinity column with 400 mM imidazole, C) Identical gel as in B) transferred to nitrocellulose membrane and probed with phage-displayed FC44 followed by anti-phage coat protein P8 antibody. Gels shown are representatives of at least three experiments showing similar results.

In order to characterize the nature of HCEC antigen(s) recognized by FC5 and FC44, the antigen/antibody complex was affinity purified using $Ni^{2+}$ affinity column. Imidazole gradient washings eluted most of the FC44/antigen complex (FIG. 11, part A). The FC44 antigen was detected by separating FC44/antigen complex on a Western blot and by exposing the membrane to FC44-c-myc-His$_5$ (His$_5$ shown in SEQ ID NO: 101) fusion protein and subsequently to anti-c-myc antibody. The antigen recognized by FC44 appeared as a triple band of approximately 36 kDa (FIG. 11, part A). A band of the same molecular weight was also detected on the silver-nitrate stained SDS-PAGE gel (FIG. 11, part B), as well as on the immunoblot membrane probed first with the phage-displayed FC44 and subsequently with the anti M13-phage coat protein (P8) antibody (FIG. 11, part C). FC44 failed to recognize any epitope in either resolved FC5/antigen complex or NC11/antigen complex. FC5 antigen (FIG. 11, part B) could not be detected using this approach indicating a possible loss of structural epitope upon denaturation.

Although the exact identity of antigen(s) recognized by FC5 and FC44 is as yet unknown, the future identification and characterization of these antigens may prove important for understanding the molecular mechanisms of transcytosis across the BBB. Moreover, identification of antigen-recognition epitopes of FC5 and FC44 will allow for 'humanizing' and/or engineering these sdAbs to the minimal effective size and maximal affinity. FC5 and FC44 sequences can then be used as a template for molecular modelling of small drugs/ligands against their respective antigens.

FC5 and FC44 have several advantages as antibody vectors over currently used/tested antibodies: i) the size of these sdAbs is half of the ScFV (~25 kDa) and 10 times smaller than any conventional IgG (150 kDa), ii) they can be expressed in high quantity in the *E. coli* periplasm (Ghahroudi et al., FEBS Letts., 414, 521-526 (1997)), an important prerequisite for production of recombinant proteins, iii) sdAbs are likely to be cleared faster from the serum and tissues than complete IgG, iv) sdAbs are shown to have a remarkable stability against high temperature, pH, and salts (Muyldermans et al., supra), and v) the non-specific interaction of sdAbs with tissues expressing high levels of Fc receptors (e.g., liver, spleen) will be low, since sdAbs lack Fc domain.

EXPERIMENTAL

Mouse melanoma, Cloudman S91, clone M-3 cells were obtained from American Type Culture Collection (Rockville, Md.). Human lung microvascular endothelial cells (HLMEC) and human umbilical vein endothelial cells (HUVEC) were purchased from Clonetics (San Diego, Calif.). The fetal human astrocytes (FHAs) were a kind gift from Dr. Jack Antel, MNI, Montreal, Canada.

All culture media and fetal bovine serum (FBS) were obtained from Gibco BRL (Gaithersburg, Md.). Endothelial cell growth supplements (ECGS), ITS™ Premix, Matrigel, and human fibronectin were purchased from Collaborative Biomedical Products (Bedford, Mass.). Human serum, gelatin, bovine serum albumin, and anti-mouse antibody conjugated to alkaline phosphatase or horse radish peroxidase were obtained from Sigma Chemical Co. (St. Louis, Mo.). Anti-phage V111 coat protein antibody and the Hi-TRAP™ column were purchased from (Amersham Pharmacia Biotech, Montreal, QC, Canada). Precast 4-12% SDS-PAGE gradient gel and colloidal gold stain were purchased from Helixx (Ontario, Canada). Silver staining kit was obtained from Bio-Rad (Ontario, Canada).

All other biochemical and molecular biology reagents were chemical grade purchased from various companies. Unless stated otherwise, the bacterial media were prepared as described (Sambrook et al., Molecular cloning: A Laboratory Manual ($2^{nd}$ ed.). Cold Spring Harbor Laboratory, Cold Spring Harbor, N.Y. (1989)). Phosphate-buffered saline (PBS) was prepared as described (Sambrook et al., supra). Induction medium was the same as Terrific Broth except that it contained no salts. Agarose top was prepared by combining the following reagents in a total volume of 1 liter: 10 g bacto-tryptone, 5 g yeast extract, 10 g NaCl, 1 g $MgCl_2.6H_2O$, and 7 g agarose. The mixture was autoclaved and stored solid at room temperature.

The oligonucleotides were synthesized using the Applied Biosystems 394 DNA/RNA synthesizer. DNA sequencing was performed by the dideoxy method [Sanger, F., Nicklen, S., and Coulson, A. R., 1992]) using the AmpliTaq DNA Polymerase FS kit and 373A DNA Sequencer Stretch (PE Applied Biosystems, Mississauga, ON, Canada). The host bacteria used for cloning was TG1: supE hsd5 thi (lac-proAB) F' [traD36 proAB⁺ lacI$^q$ lacZ M15]. All the cloning steps were performed as described (Sambrook et al., supra). The vector fd-tet was purchased from American Type Culture Collection (Manassas, Va.) and engineered such that it contained ApaI and NotI restriction sites immediately following the gIIIp leader sequence codons (Simon J. Foote, personal communications).

Construction of Naive Llama sdAb Library

Total RNA was isolated from the leukocytes of freshly-drawn heparinized blood of a male Llama (Lama glama) using QIAamp RNA Blood Mini™ kit (QIAGEN, Mississauga, ON, Canada) and following the recommended protocol. The concentration of RNA was calculated by measuring the A260 value and assuming 1 A260=40 µg/ml. Reverse transcription-polymerase chain reaction (RT-PCR) was performed on a total of 5.3 µg RNA using the HotStarTaq Polymerase™ kit (QIAGEN). The primers used included a CH2-specific primer, LlamaFOR, 5'(CGCCATCAAGGTACCAGTTGA)$_3$' [SEQ ID No: 88] and LlamaBACK primer, 5'(GATGTGCAGCTGCAG-GCGTCTGGRGGAGG)3' [SEQ ID No: 89], which anneals to the 5' flanking region of VH genes. Amplified product of approximately 600 base pair was purified from the agarose gel using QIAquick Gel Extraction™ kit (QIAGEN) and subjected to a second round of PCR using the primers LlamaApaII, 5'(CATGACCACAGTGCACAG-GAKGTSCAGCT)3' [SEQ ID No: 90] and LlamaNotI, 5'(CGATTCTGCGGCCGCTGAGGAGACGGTGACCTG)

3' [SEQ ID No: 91]. The PCR mixture contained 10 pmol/μl each of the two primers, 1× buffer (Perkin Elmer), 200 μM each of the four dNTPs and 0.05 unit/μl AmpliTaq™ DNA polymerase (Perkin Elmer). PCR protocol consisted of an initial denaturation step at 95° C. for 15 min followed by 35 cycles of 94° C. for 30 sec, 45° C. for 30 sec, and 72° C. for 1 min, and a final extension step at 72° C. for 10 min. The primers were complimentary to the 5' and 3' ends of the amplified product and incorporated ApaII and NotI restriction sites (underlined) at the end of VH genes. The amplified products were purified using QIAquick PCR Purification Kit™ (QIAGEN), cut sequentially with ApaII and NotI restriction endonucleases, purified again, ligated to the ApaII/NotI-treated fd-tet phage vector and desalted using the above kit. Electrocompetent TG1 cells were prepared [Tung, W. L. and Chow, K. C., 1995]) and 1.5 μg of the ligated product was mixed with 40 μl of competent $E. coli$ strain TG1 and the cells were transformed by electroporation using the BIO-RAD Gene Pulser™ according to the manufacturer's instructions. The transformed cells were immediately transferred into 1 ml of SOC medium and split into 3 sterile tubes containing 3 ml of 50° C. agarose top, vortexed immediately, poured onto pre-warmed 2×YT Petri dishes, and incubated at 37° C. overnight. The phage particles were eluted by adding five ml of sterile PBS to the plates gently shaken at 4° C. for 3 hr. The phage-containing PBS was collected, the plates were rinsed with an additional 5 ml PBS and the two supernatants were combined in a centrifuge bottle. The contents were centrifuged at 6000 g for 15 min at 4° C., the supernatant was decanted into a sterile centrifuge bottle and the phage was purified as described (Harrison et al., supra). At the end of the purification, the phage pellet was dissolved in 20 ml of sterile PBS and stored in liquid nitrogen in 100 μl aliquots.

To determine the size of the library, immediately following the transformation and after the addition of the SOC medium, a small aliquot of the electroporated cells was serially diluted in exponentially growing TG1 cells. 200 μl of the diluted cells was mixed with 3 ml of 50° C. agarose top and immediately poured onto 2×YT plates pre-warmed to 37° C. Plates were incubated overnight at 37° C. and the number of plaques was used to determine the size of the library.

Cell Culture

Human cerebromicrovascular endothelial cells (HCEC) and human pial arterial endothelial cells (HPEC) were isolated using a modification (Stanimirovic et al., J. Cell. Physiol., 169, 455-467 (1996)) of the procedures described by Gerhart et al. (Brain Res. Bull., 21, 785-793 (1988)). Capillaries and microvessels derived from small samples of human temporal lobe excised surgically from patients treated for idiopathic epilepsy were enzymatically dissociated and used to initiate endothelial cultures in growth media (Earle's salts, 25 mM Hepes, 4.35 g/l sodium bicarbonate and 3 mM L-glutamine), 10% fetal bovine serum (FBS), 5% human serum, 20% murine melanoma cell (mouse melanoma, Cloudman S91, clone M-3, melanin producing cells)-conditioned media, 5 μg/ml of insulin, 5 μg/ml of transferrin, 5 ng/ml selenium, and 10 μg/ml of endothelial cell growth supplement (ECGS), (Stanimirovic et al., supra). The human lung microvascular endothelial cells (HLMEC) and human umbilical vein endothelial cells (HUVEC) were grown and subcultured in the media supplied by the Clonetics (San Diego, Calif.). The primary fetal human astrocyte cultures (FHAs) were grown in Dulbeco's modified Eagle's medium (DMEM) supplemented with 4.5 g/L glucose, 2 mM glutamine, 10% FBS, and 25 g/ml gentamycin. All cell cultures were maintained at 37° C. in an atmosphere of 5% $CO_2$ in air.

Differential Panning on Human Endothelial Cells

A phage displayed llama single domain antibody library with a functional size of $5.6 \times 10^8$ was used for panning Subcultured HLMEC and HCEC (passages 2-6; ~1 million cells) were used as bait in each round of panning. The endothelial cells were washed three times in PBS, scraped, counted and blocked by re-suspending the cells in 100 μl of PBS containing 1% bovine serum albumin (BSA) solution. Following a 30 min blocking, $10^{12}$ phage transducing units in 1% BSA-PBS were added to the HLMEC and allowed to bind for 1 h at 37° C. The HLMEC were then centrifuged for 5 minute at 1000 rpm and the supernatant containing the unbound phage was collected and added to the HCEC (100 μl final volume). After 1 h incubation at 37° C., HCEC were washed 6 times with ice cold PBS (200 μl) with a short centrifugation (1000 rpm) between the washes. The phage bound to HCEC was stripped from the cell surface in 3 consecutive steps (designated 51, S2, S3) using a 500 nl of stripping buffer [50 mM glycine pH 2.8, 0.5 M NaCl, 2 M urea, and 2% polyvinyl pyrolydine (PVP)](Becerril et al., Biochem. Biophys. Res. Commun., 255, 386-393 (1999)). The stripping buffer containing phage dislocated from HCEC was collected and neutralized with half volume of 1M Tris pH 7.4 buffer.

Immediately following 3 stripping rounds, the phage internalized into HCEC (designated INT) was extracted using 200 μl of lysis buffer (100 mM Triethanolamine). Lysis buffer containing internalized phage was collected and neutralized as above.

Approximately 400 μl of S3 and 150 μl of INT phage fractions were subsequently used to infect 10 ml of exponentially growing TG1 culture and allowed to amplify at 37° C. for 30 min. Serial dilutions of the infected cells were then used to determine the titre of the phage present in each fraction. 200 μl of the serially diluted cells were mixed with 3 ml of 45° C. agarose top and immediately poured onto pre-warmed 2×YT plates and incubated overnight at 37° C. The remainder of the infected cells were spun down and resuspended in 900 μl 2×YT, divided in 3×300 μl aliquots, mixed with 3 ml agarose top and the phage were plated for overnight propagation at 37° C. The propagated phage particles were then eluted by adding 5 ml of sterile PBS while gently shaking plates at 4° C. for 3 h. The phage-containing PBS was then collected; the plates were rinsed with an additional 5 ml PBS and two supernatants were combined in a centrifuge bottle. The contents were centrifuged at 6000 g for 15 min at 4° C., the supernatant was decanted into a sterile centrifuge bottle and the phage was purified as described (Harrison et al., Methods Enzymol., 37, 579-590 1996). The phage titre was determined, and a total of $10^{12}$ transducing phage units from a S3 fraction of the first panning (1S3) were used for the second round of selection. The third and fourth panning were performed using $10^{12}$ transducing units of 2S3 and 3S1 phage fractions, respectively.

Plaque PCR

During each round of panning the plaques from the titre plates were randomly chosen for PCR analysis. After a brief vortexing of the plaque in a 50 μl of H2O, a 1 μl was used as template for PCR amplification using the primers llama ApaII, 5'(CATGACCACAGTGCACAGGAKGTSCAGCT) 3' [SEQ ID NO: 90] and llama NotI, 5'(CGATTCTGCGGC-CGCTGAGGAGACGGTGACCTG)3' [SEQ ID NO: 91]. The PCR mixture contained 10 μmol/g1 each of the two primers, 1× buffer (Perkin Elmer, Mississauga, ON, Canada), 200 04 each of the four dNTP's and 0.05 unit/μl AmpliTaq™ DNA polymerase (Perkin Elmer, Mississauga, ON, Canada). PCR protocol consisted of an initial denaturation step at 95° C. for 15 min followed by 35 cycles of 94° C. for 30 s, 45° C.

for 30 s, and 72° C. for 1 min, and a final extension step at 72° C. for 10 min. The amplified products were run on 1% agarose gel; enrichments were assessed by the percent of plaques that yielded a 600 bp full length gene product.

Sequencing

Selected phage clones were PCR amplified using the same set of primers and condition used for colony (plaque) PCR. The amplified products were purified with QIAquick Gel Extraction™ kit (QIAGEN), and sequenced by the dideoxy method (Sanger et al., 1977) using the AmpliTaq DNA Polymerase FS kit. Analysis was done using 373A DNA Sequencer Stretch (PE Applied Biosystems, Mississauga, ON, Canada).

Construction and purification of c-myc-His$_5$-sdAb fusion proteins (His$_5$ shown in SEQ ID NO: 101)

Genes of phage-displayed single domain antibodies (sdAb) selected by differential panning and enrichment procedures described above were amplified out of the phage vector by PCR using the primers, VH.Bbs, 5'(TATGAAGACACCAGGCCGATGTGCAGCTGCAGGCG)3', [SEQ ID No: 92] and VH.Bam, 5'(TATGGATCCTGAGGAGACGGTGACCTG)3' [SEQ ID No: 93] that introduced BbsI and BamHI sites at the ends of the amplified fragments. sdAb genes were subsequently purified, cut sequentially with BbsI and BamHI restriction endonucleases, purified again with QIAquick Gel Extraction™ kit (QIAGEN, Mississauga, ON, Canada), and ligated to the BbsI/BamHI-treated pSJF-2 vector. An aliquot of the ligated product was used to transform *E. coli* strain TG1. Transformants were selected on ampicillin plates and the clones harbouring the sdAb genes were identified by PCR and sequencing. For expression, single positive clones were used to inoculate 25 ml of LB containing 100 µg/ml ampicillin and the culture was shaken at 240 rpm at 37° C. overnight. The entire overnight culture was used to inoculate 1 liter of M9 medium supplemented with 5 µg/ml vitamin B1, 0.4% casamino acid and 100 µg/ml ampicillin. The culture was shaken at room temperature for 30 h at 180 rpm and subsequently supplemented with 100 ml of 10× induction medium and 100 µl of 1 M isopropylthio-D-galactoside (IPTG). The culture was shaken for another 60 h and the periplasmic fraction was extracted by osmotic shock method (Anand et al., Gene, 100, 39-44 (1991)). The periplasmic fraction was dialyzed extensively in 10 mM HEPES buffer pH 7.0, 500 mM NaCl.

The presence of the C-terminal His$_5$ tag (SEQ ID NO: 101) in sdAbs allowed for one step protein purification by immobilized metal affinity chromatography using HiTrap Chelating™ column. The 5-ml column was charged with Ni$^{2+}$ by applying 30 ml of a 5 mg/ml NiCl$_2$.6H$_2$O solution and subsequently washed with 15 ml deionized water. Purification was carried out as described (MacKenzie et al., Biotechnology, 12, 390-395 (1994)) except that the starting buffer was 10 mM HEPES buffer, 10 mM imidazole, 500 mM NaCl, pH 7.0. The bound protein was eluted with a 10-500 mM imidazole gradient. The purity of the protein was determined by SDS-PAGE (Laemmli U.K., Nature, 227, 680-685 (1970)).

Binding and uptake of sdAb-c-myc-His$_5$ fusion proteins (His$_5$ shown in SEQ ID NO: 101) The sdAbs were labeled with alexafluor 488/532 (Molecular Probes, Ontario, Canada) and purified on a gel filtration column as per the manufacturer protocol.

The plasma membrane fraction of the HCEC was prepared using a detergent free density gradient medium OptiPrep™ (Nycomed Pharma AS, Norway). The membrane vesicles were prepared by sonication (50J/W per sec each time) and purified as described (Smart et al., Proc. Natl. Acad. Sci. USA, 92, 10104-10108 (1995)). The membranes and vesicles were applied onto a coverslip and air dried before the addition of Alexafluor 488/532-labeled sdAb. After 1 h of incubation, the coverslips were rinsed with PBS and imaged using an Olympus fluorescence microscope.

To determine the uptake of FC44, FC5 and NC11 into live cells, HCEC and HLMEC were plated onto glass coverslips in 24 well dishes. Cells were incubated with the Alexafluor 488/532-labeled sdAbs for up to 3 h in PBS at 37° C. and in some cases at 22° C. and 4° C. Cells were then washed 2 times in PBS and examined using confocal/fluorescence microscopy. The viability of cell subjected to the described treatments was assessed by propidium iodide staining of cell nuclei (Stanimirovic et al., Glia, 19, 123-134 (1997)).

Transmigration Studies in in Vitro BBB Model

HCEC were seeded at 3×10$^5$ cells/cm$^2$ on a 0.5% gelatin coated Falcon tissue culture inserts (pore size-1 µm; surface area 0.83 cm$^2$) in 1 ml of growth medium. The bottom chamber of the insert assembly contained 2 ml of growth medium supplemented with the fetal human astrocyte (FHAs)-conditioned medium in a 1:1 (v/v) ratio (Muruganandam et al., supra). The FHAs-conditioned medium was obtained by incubating confluent FHAs in a serum free M199 for 72 h. The transendothelial electrical resistance (TEER) of the endothelial cell monolayers was measured using Endohm™ electrical resistance apparatus (World Precision Instruments, Sarasota, Fla.).

All transport experiments were performed in transport buffer (HBSS containing 5 mM glucose/10 mM HEPES pH 7.4/0.05% BSA) after equilibrating the cells for 30 min at 37° C. The barrier integrity was assessed by measuring the passage sodium fluorescein (MW 376 Dalton 25 µg/ml), fluorescently-labeled dextran (MW 10 kDa), and $^{14}$C dextran-carboxyl (MW 70 kDa) across triplicate HCEC monolayers, and across 0.5% gelatin coated inserts without cells. Samples were collected from the bottom chambers from 5 min to 90 min period. The fluorescence was measured in a Cytofluor 2350, Millipore, Ont, Canada and the radioactive counts were measured in Wallac microbeta liquid scintillation counter (Turku, Finland). Clearance values were determined using previously described protocols (Dehouck et al., J. Neurochem., 58, 1790-1797 (1992); Pardridge et al., J. Pharmacol. Exp. Therap., 253, 884-891 (1990)).

The selection of BBB-transmigrating phage clones was done by adding amplified library containing 10$^{11}$ transducing phage enriched for HCEC binding (4S3) and internalizing species (41NT) to the upper compartment and by determining the PFU's in 10 µl out of 25 µl aliquots collected from the bottom compartment at specified time points.

The ability of purified soluble FC44, FC5, and NC11 (negative control) fusion proteins to transmigrate across in vitro human BBB model was assessed by adding 100 µg of fusion protein into the upper compartment. At selected time points, 200 µl of the sample from the bottom compartment was collected and the concentration of the respective sdAb in the bottom chamber was quantified by a Nickel-trap ELISA as described below.

Enzyme-Linked Immunosorbent Assays (ELISA)

ELISA against phage coat protein P8 (phage ELISA) was used to determine the binding of selected phage clones to various human endothelial cells in culture. Individual phage-infected TG1 colonies were used to inoculate 200 µl of Luria broth (LB) in sterile 96-well plates. The cells were grown overnight gently shaken at 100 rpm at 37° C. The plates were then spun down, and the phage-containing supernatants were used for phage ELISA as described below. Briefly, monolayers of HCEC and HLMEC grown in 96 well plates were blocked at room temperature by adding 300 µl of PBS-2%

BSA for 1 h. The contents of the wells were aspirated, 100 µl of phage supernatant in 2% BSA-PBS was added, and cells were incubated at 37° C. for 1 h. After removing the supernatants, the cells were washed 6 times with PBS-0.05% (v/v) Tween-20 and then incubated with 100 µl of a 1:1000 dilution of HRP-conjugated anti-M13 monoclonal antibody in 2% BSA-PBS at 37° C. for 1 h. The cells were washed 6 times and the binding of phage to the cell surface was detected colorimetrically by adding 100 µl of the TMB peroxidase substrate and $H_2O_2$ (KPL, Maryland, USA) mixture at room temperature. The reaction was terminated by adding 100 µl of 1 M $H_3PO_4$ and the optical density (O.D) was read at 450 nm using DYNATECH MR5000ELISA plate reader (Dynatech Laboratories, Chantilly, Va., USA). Wild type phage was used for determining a non-specific binding.

ELISA against c-myc tag was used to determine binding of purified sdAb-c-myc-$His_5$ ($His_5$ shown in SEQ ID NO: 101) fusion proteins to cells or cell lysates. The recombinant sdAb (100 µg/ml) fused with the c-myc tag were incubated with the live HCEC and HLMEC grown in 96 well-plates, or with the cell extracts from HCEC, HPEC, FHAs, HUVEC and HLMEC for 1 h at 37° C. After washing to remove unbound sdAb-c-myc fusion protein, the bound protein was detected using mouse anti-c-myc antibody conjugated to HRP (1:5000 dilution).

A nickel trap ELISA was used to determine the concentration of purified FC5, FC44, and NC11 fusion proteins in the BBB transmigration assay. Briefly, the sample aliquots from the bottom chambers of the in vitro BBB model were allowed to incubate overnight in a 96 format wells of Ni-NTA H isSorb strips (Qiagen Inc, Mississauga, ON, Canada) with constant shaking. After blocking the wells with 2% BSA-PBS, the concentration of $His_5$-sdAbs ($His_5$ shown in SEQ ID NO: 101) trapped onto the Ni-NTA H isSorb was detected using an HRP-conjugated anti-c-myc antibody (1:5000 dilution). The concentration was determined from standard curve constructed using respective pure sdAbs.

In Vivo Biodistribution of the FC5 and FC44

Five to six week old C57BL/6 mice (approx. 18 g) were injected in the tail vein with phage-displayed FC5, FC44 or wild type phage ($10^9$ pfu/mouse in 100 µl for each library). Separate groups of animals were injected in the tail vein with 30 µg/mouse of FC5, FC44 or NC11 fusion proteins with c-myc-$His_5$ ($His_5$ shown in SEQ ID NO: 101). Four hours after injection, the animals were anesthetized with 0.27 ml/100 g of Hypnorm/Versad i.p. and perfused through the heart with 50 ml of saline. Brain, liver, lung and kidney were dissected, snap-frozen in dry ice and stored at −80° C.

Phage titers and immunoblot analyses in these tissues were done after homogenizing a pre-weighed tissues in 0.5 ml PBS containing 10 µg/ml of protease inhibitors using FastPrep® FP 120 instrument. For determining phage titers, known amounts of tissue extract (0.2 to 10 µl) were used for infecting the bacteria and titers were determined as described above. For immunoblot, tissue was homogenized and 500 µg of the protein from the tissue extracts was affinity purified using His Microspin™ purification module. After desalting the final eluate, samples were dried in a vacuum concentrator, resuspended in 80 µl of SDS-PAGE sample buffer, and run on 10% SDS-PAGE.

Affinity Purification of the Antigen

HCEC grown in 100 mm tissue culture dishes were rinsed and scraped into PBS cooled to 4° C. The cells were briefly sonicated in a bucket sonicator for 3 min in the presence of 0.05% Triton-X 100 and 10 µg/ml protease inhibitors and, after determining the protein content in the cell lysates by the method of Bradford (Anal. Biochem, 72, 248-254 (1976)) the antigen was affinity purified using His Microspin™ purification module (Amersham Pharmacia Biotech, Quebec, Canada). A known amount of protein was loaded on to a nickel-charged chelating sepharose microspin column previously adsorbed with $His_5$ (SEQ ID NO: 101) tagged fusion sdAb. Sequential washing and elution was done using increasing strengths (20 mM, 100 mM and 400 mM) of the imidazole/salt elution buffer.

Immunoblot

Immunoblot analysis was used to determine the presence of sdAb fusion proteins in tissue extracts after in vivo injection, and the expression of the antigen in HCEC. The affinity purified tissue extracts and antigen-sdAbs complexes were mixed with an equal volume of gel loading buffer (50 mM Tris-HCl pH 6.8, 100 mM DDT, 2% SDS, 0.1% bromophenol blue, 10% glycerol), boiled for 3 min and loaded onto a 4-12% or 12% SDS polyacrylamide gels. The proteins separated on the gel were subsequently electrophoretically transferred onto a nitrocellulose membrane using a Bio-Rad mini transblot cell apparatus. The membranes were blocked with PBS-BSA for 1 h.

For sdAbs detection in mouse tissues, the membranes were incubated with monoclonal anti-c-myc IgG antibody (1:1000) for 30 min, washed and then incubated with secondary anti-mouse IgG antibody conjugated to alkaline phosphatase for 30 min.

For HCEC antigen detection, a separate gel was silver stained using the Silver plus kit (BioRad). Nitrocellulose membranes were incubated with phage carrying selected sdAbs ($10^9$ pfu) or with 30 µg of purified selected sdAbs for 1 h at room temperature under constant agitation. After washing (3×5 min) in PBS containing 0.05% Tween-20, the membranes were incubated with monoclonal anti-c-myc IgG antibody (1:1000) for 0.5 h or with anti-M13 phage antibody. The membranes were then washed 3×5 min in PBS and incubated with secondary anti-mouse IgG antibody conjugated to alkaline phosphatase for 0.5 hour.

The protein bands were visualized using the alkaline phosphatase substrates, 5-bromo-4-cholro-3 indolyl phosphate and nitroblue tetrazolium (Sigma Chemical Company, St. Louis Mo.).

Although various particular embodiments of the present invention have been described hereinbefore for the purpose of illustration, it would be apparent to those skilled in the art that numerous variations may be made thereto without departing from the spirit and scope of the invention, as defined in the appended claims.

What is claimed is:

1. An isolated antibody fragment comprising:
   a CDR1/H1 region sequence selected from the group consisting of VRTFSIYAMG (SEQ ID NO: 94), GFKITHYTMG (SEQ ID NO: 95), and VRTFSIYAIG (SEQ ID NO: 96);
   a CDR2/H2 region sequence selected from the group consisting of GINRSGDVTKYADFVKG (SEQ ID NO: 97) and RITWGGDNTFYSNSVKG (SEQ ID NO: 98); and
   a CDR3/H3 region sequence selected from the group consisting of TWAYDTVGALTSGYNF (SEQ ID NO: 99) and GSTSTATPLRVDY (SEQ ID NO: 100),
   wherein said antibody fragment selectively binds to an antigen on the surface of mammalian cells expressing blood-brain barrier antigens and transmigrates across a blood-brain barrier.

2. The isolated antibody fragment according to claim 1, wherein the CDR1/H1 sequence is GFKITHYTMG (SEQ ID NO: 95), the CDR2 sequence is RITWGGDNTFYSNSVKG (SEQ ID NO: 98), and the CDR3 sequence is GSTSTATPLRVDY (SEQ ID NO: 100).

3. The isolated antibody fragment according to claim 1, wherein the CDR1 sequence is VRTFSIYAMG (SEQ ID NO: 94), the CDR2 sequence is GINRSGDVTKYADFVKG (SEQ ID NO: 97), and the CDR3 sequence is TWAYDTVGALTSGYNF (SEQ ID NO: 99).

4. The isolated antibody fragment according to claim 1, wherein the CDR1 sequence is VRTFSIYAIG (SEQ ID NO: 96), the CDR2 sequence is GINRSGDVTKYADFVKG (SEQ ID NO: 97), and the CDR3 sequence is TWAYDTVGALTSGYNF (SEQ ID NO: 99).

5. The isolated antibody fragment according to claim 1, wherein the mammalian cells are human cerebromicrovascular endothelial cells.

6. The isolated antibody fragment according to claim 5, which is internalized by the cerebromicrovascular endothelial cells.

7. The isolated antibody fragment according to claim 1, which comprises at least a part of a variable heavy domain of a llama antibody.

8. The isolated antibody fragment according to claim 7, wherein amino acid residues of the VL interface of the variable heavy domain are Glu at position 44, Arg at position 45 and Phe at position 47 based on Kabat numbering of the variable heavy domain.

9. The isolated antibody fragment according to claim 1, which is selected from the group consisting of SEQ ID NO: 85, SEQ ID NO: 86 and SEQ ID NO: 87.

10. A therapeutic or diagnostic agent, said agent comprising the isolated antibody fragment according to claim 1 linked to a therapeutic or diagnostic entity.

11. A therapeutic or diagnostic agent according to claim 10, wherein the mammalian cells are human cerebromicrovascular endothelial cells.

12. A therapeutic or diagnostic agent according to claim 11, wherein the antibody fragment is internalized by the cerebromicrovascular endothelial cells.

13. A therapeutic or diagnostic agent according to claim 10, wherein the agent is formulated for administration by an intravenous, intraperitoneal, intramuscular, or subcutaneous injection.

14. A therapeutic or diagnostic agent according to claim 10, wherein the agent is localized in brain parenchyma after administration.

15. A therapeutic or diagnostic agent according to claim 10, wherein the antibody fragment comprises at least a part of a variable heavy domain of a llama antibody.

16. A therapeutic or diagnostic agent according to claim 10, wherein the antibody fragment is selected from the group consisting of SEQ ID No. 85, SEQ ID No. 86 and SEQ ID No. 87.

17. A therapeutic or diagnostic agent according to claim 10, wherein the therapeutic or diagnostic entity is a peptide.

18. A therapeutic or diagnostic agent according to claim 10, wherein the therapeutic or diagnostic entity is a piece of DNA.

19. A therapeutic or diagnostic agent according to claim 10, wherein the therapeutic or diagnostic entity is a phage.

20. A therapeutic or diagnostic agent according to claim 10, wherein the therapeutic or diagnostic entity is a fluorescent or radioactive label.

21. The therapeutic or diagnostic agent of claim 10, wherein the therapeutic or diagnostic entity is linked directly or indirectly to the agent comprising the antibody fragment.

22. The therapeutic or diagnostic agent of claim 10, wherein the therapeutic or diagnostic entity is linked covalently or non-covalently to the agent comprising the antibody fragment.

* * * * *